US006815514B2

United States Patent
Andell et al.

(10) Patent No.: US 6,815,514 B2
(45) Date of Patent: Nov. 9, 2004

(54) CATALYSTS

(75) Inventors: Ove Andell, Helsinki (FI); Janne Maaranen, Kerava (FI); Jouni Hoikka, Hamari (FI); Tiina Vanne, Helsinki (FI); Soile Rautio, Porvoo (FI)

(73) Assignee: Borealis Technology Oy, London (GB)

( * ) Notice: Subject to any disclaimer, the term of this patent is extended or adjusted under 35 U.S.C. 154(b) by 0 days.

(21) Appl. No.: 10/344,855

(22) PCT Filed: Aug. 21, 2001

(86) PCT No.: PCT/GB01/03757

§ 371 (c)(1),
(2), (4) Date: May 28, 2003

(87) PCT Pub. No.: WO02/16374

PCT Pub. Date: Feb. 28, 2002

(65) Prior Publication Data

US 2003/0225275 A1 Dec. 4, 2003

(30) Foreign Application Priority Data

Aug. 21, 2000 (GB) ............................................. 0020613

(51) Int. Cl.⁷ ............................... C08F 4/44; C07F 7/02
(52) U.S. Cl. ....................... 526/160; 526/161; 526/943; 502/152; 502/155; 502/167; 544/229; 556/53
(58) Field of Search ................................ 526/160, 161, 526/943; 502/152, 155, 167; 544/229; 556/53

(56) References Cited

U.S. PATENT DOCUMENTS 6,365,688 B1 * 4/2002 Andell et al. ............... 526/160

FOREIGN PATENT DOCUMENTS

| WO | WO 96/13529 | 5/1996 |
| WO | WO 98/04570 | 2/1998 |
| WO | WO 98 40420 | 9/1998 |
| WO | WO 01/70395 | 9/2001 |

OTHER PUBLICATIONS

Chen, "The Syntheses and Mass Spectra of Some N–Substituted Ferrocenylmethyl Adenines", Journal of Organometallic Chemistry 202:183–189 (1980).

Houlton et al, "Synthesis, structure and redox properties of ferrocenylmethylnucleobases", J. Chem. Soc., Dalton Trans. (18):3229–3234 (1999).

Nekrasov et al, "Ferrocenylalkylation of nucleic acid bases", Ross. Khim. ZH 41(4):117–120 (1997)—Abstract.

* cited by examiner

Primary Examiner—Robert D. Harlan
(74) Attorney, Agent, or Firm—Nixon & Vanderhye P.C.

(57) ABSTRACT

The invention describes ligands of formula (I), wherein LIG represents an $\eta^5$-ligand substituted by a group $R_1$ and a group $(R")_m$; X represents a 1 to 3 atom bridge; Y represents a nitrogen or phosphorus atom; Z represents a carbon, nitrogen or phosphorus atom.

23 Claims, No Drawings

CATALYSTS

This invention relates to catalysts for olefin polymerisation, in particular to catalyst compounds containing metals η-bonded by $\eta^5$-ligands, e.g. cyclopentadienyl ligands and η or σ-bonded by a bicyclic nitrogen ligand, and their use in olefin polymerisation.

In olefin polymerization, it has long been known to use as a catalyst system the combination of a metallocene procatalyst and an alumoxane or boron based co-catalyst.

By "metallocene" is here meant an η-ligand metal complex, e.g. an "open sandwich" or "half sandwich" compound in which the metal is complexed by a single η-ligand, a "sandwich" compound in which the metal is complexed by two or more η-ligands, a "handcuff" compound" in which the metal is complexed by a bridged bis-η-ligand or a "scorpionate" compound in which the metal is complexed by an η-ligand linked by a bridge to a σ-ligand.

Metallocene procatalysts are generally used as part of a catalyst system which also includes an ionic cocatalyst or catalyst activator, for example, an aluminoxane (e.g. methylaluminoxane (MAO), hexaisobutylaluminoxane and tetraisobutylaluminoxane) or a boron compound (e.g. a fluoroboron compound such as triphenylpentafluoroboron or triphenylcarbenium tetraphenylpentafluoroborate (($C_6H_5)_3$ $B^+B^-(C_6F_5)_4$))

Alumoxanes are compounds with alternating aluminium and oxygen atoms generally compounds of formula

or

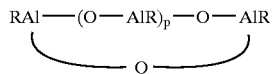

where each R, which may be the same or different, is a $C_{1-10}$ alkyl group, and p is an integer having a value between 0 and 40). These compounds may be prepared by reaction of an aluminium alkyl with water. The production and use of alumoxanes is described in the patent literature, especially the patent applications of Texas Alkyls, Albemarle, Ethyl, Phillips, Akzo Nobel, Exxon, Idemitsu Kosan, Witco, BASF and Mitsui.

Traditionally, the most widely used alumoxane is methylaluminoxane (MAO), an alumoxane compound in which the R groups are methyls. MAO however is poorly characterised and relatively expensive and efforts have been made to use alumoxanes other than MAO. Thus, for example WO98/32775 (Borealis) proposes the use of metallocene procatalysts with alumoxanes in which R is a $C_{2-10}$ alkyl group, eg hexaisobutylalumoxane (HIBAO). However, such metallocenes generally have poor catalyst activities with non-MAO alumoxanes.

Since each polymerisation catalyst gives rise to polymer products with slightly differing properties, there remains an ongoing search for new and improved olefin polymerisation catalysts.

We have now surprisingly found that a single site procatalyst system based on a $\eta^5$-ligand, e.g. cyclopentadienyl type ligand and a η or σ-bonding bicyclic nitrogen ligand may be used very effectively in polymerisation catalysis, especially in the manufacture of polyethylene or polypropylene.

Thus viewed from one aspect the invention provides a compound of formula (I) comprising

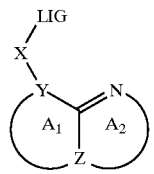

wherein

LIG represents an $\eta^5$-ligand substituted by a group $R_1$ and a group $(R")_m$;

X represents a 1 to 3 atom bridge, optionally substituted, e.g. by R" groups;

Y represents a nitrogen or phosphorus atom;

Z represents a carbon, silicon, nitrogen or phosphorus atom;

the ring denoted by $A_1$ is an optionally substituted, optionally saturated or unsaturated 5 to 12 membered heterocyclic ring;

the ring denoted by $A_2$ is an optionally substituted, unsaturated 5 to 12 membered heterocyclic ring;

$R_1$ represents hydrogen, R" or a group $OSiR'_3$;

each R', which may be the same or different is a $R^+$, $OR^+$, $SR^+$, $NR^+_2$ or $PR^+_2$ group where each $R^+$ is a $C_{1-16}$ hydrocarbyl group, a tri-$C_{1-8}$ hydrocarbylsilyl group or a tri-$C_{1-8}$hydrocarbylsiloxy group, preferably R' being a $C_{1-12}$ hydrocarbyl group, e.g. a $C_{1-8}$ alkyl or alkenyl group;

each R", which may be the same or different is a ring substituent which does not form a σ-bond to a metal η-bonded by the bicyclic ring, eg it may be hydrogen, $R^+$, $OR^+$, $SR^+$, $NR^+_2$ or $PR^+_2$ group where each $R^+$ is a $C_{1-16}$ hydrocarbyl group, a tri-$C_{1-8}$ hydrocarbylsilyl group or a tri-$C_{1-8}$hydrocarbylsiloxy group; and m is zero or an integer between 1 and 3.

Viewed from a further aspect the invention provides an olefin polymerisation catalyst system comprising or produced by reaction of (1) a metallated compound as hereinbefore defined (from hereon called a procatalyst) and (2) a cocatalyst, e.g. an aluminium alkyl compound or boron compound, in particular an alumoxane, especially an aluminium alkyl compound comprising alkyl groups containing at least two carbon atoms.

Viewed from a still further aspect the invention provides a process for olefin polymerisation comprising polymerising an olefin in the presence of a catalyst system as hereinbefore described.

Viewed from a yet further aspect the invention provides a process for the preparation of a procatalyst, said process comprising metallating with a group 3 to 7 transition metal a compound of formula (I)

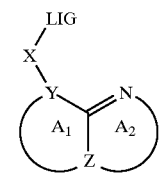

wherein LIG, X, Y, Z and rings $A_1$ and $A_2$ are as hereinbefore defined.

Viewed from a further aspect the invention provides the use of a procatalyst as hereinbefore defined in olefin polymerization, especially ethylene or propylene polymerisation or copolymerisation.

Viewed from a yet further aspect the invention provides an olefin polymer produced by a polymerisation catalysed by a procatalyst compound as hereinbefore defined.

The compounds of formula (I) as hereinbefore described may be coupled with a metal from groups 3 to 7. By group 3 (etc) metal is meant a metal in group 3 of the Periodic Table of the Elements, namely Sc, Y, etc. It is preferable if the metal coupling the compound of the invention is in the $III^+$ oxidation state, although metals in the $II^+$ and $IV^+$ oxidation states are also advantageous. The metal employed in the catalyst system of the invention is most preferably from groups 4, 5 or 6 of the periodic table, e.g. Cr, Mo, W, Ti, Zr, Hf, V, Nb or Ta. Most especially the metal is Cr or Ti, e.g. $Cr^{3+}$ or $Ti^{3+}$.

Where the metal is Cr, it has surprisingly been found that the catalyst system of the invention is capable of making polypropylene as a powder.

The group 3 to 7 metal in the metallated procatalyst of the invention coordinates to the $\eta^5$-ligand and σ or η bonds to certain atoms in the bicyclic nitrogen ligand. Where the metal forms sigma bonds with the bicyclic nitrogen ligand, only atoms Z and N can coordinate to the metal. Thus, the metal may be coordinated only to atom X, only to N or to both the Z and N atoms. The Y atom is therefore not involved in coordination with the metal.

However, if an η ligand is formed between the metal and bicyclic nitrogen group then coordination to any double bond present in bicyclic nitrogen ligand is possible. Such η bonds may be $\eta^2$ or $\eta^3$ depending on the nature of the bicyclic nitrogen ligand. The metal may also be coordinated by hydrogen atoms, hydrocarbyl σ-ligands (eg optionally substituted $C_{1-12}$ hydrocarbyl groups, such as $C_{1-12}$ alkyl, alkenyl or alkynyl groups optionally substituted by fluorine and/or aryl (eg phenyl) groups), by silane groups (eg $Si(CH_3)_3$), by halogen atoms (eg chlorine), by $C_{1-8}$ hydrocarbylheteroatom groups, by tri-$C_{1-8}$hydrocarbylsilyl groups, by bridged bis-σ-liganding groups, by amine (eg $N(CH_3)_2$) or imine (eg N=C or N=P groups, eg $(iPr)_3P=N$) groups, or by other σ-ligands known for use in metallocene (pro) catalysts.

By a σ-ligand moiety is meant a group bonded to the metal at one or more places via a single atom, eg a hydrogen, halogen, silicon, carbon, oxygen, sulphur or nitrogen atom.

Examples of σ-ligands include halogenides (e.g. chloride and fluoride), hydrogen,
tri$C_{1-12}$ hydrocarbyl-silyl or -siloxy(e.g. trimethylsilyl),
tri$C_{1-6}$ hydrocarbylphosphimido (e.g. triisopropylphosphimido),
$C_{1-12}$hydrocarbyl or hydrocarbyloxy (e.g. methyl, ethyl, phenyl, benzyl and methoxy),
di$C_{1-6}$ hydrocarbylamido (e.g. dimethylamido and diethylamido), and
5 to 7 ring membered heterocyclyl (eg pyrrolyl, furanyl and pyrrolidinyl). Preferable σ ligands include halogens, alkyls, or chloro-amido groups.

Y preferably represents a nitrogen atom.

In the catalyst system formed from the compound of the invention, the Y atom does not sigma coordinate to the metal ion. Instead, the atom at Y serves to provide an atom whereby the bridging group X can join the bicyclic nitrogen group to the $\eta^5$-ligand.

The Z atom, which as mentioned above may be involved in coordination with the metal ion, is preferably a phosphorus or nitrogen atom, especially a nitrogen atom.

In a most preferred embodiment both Y and Z are nitrogen.

The A rings ($A_1$ and $A_2$), formed partially from the atoms —Y—C—Z— or —N—C—Z— may be or different sizes but are preferably or the same size. Moreover, each ring preferably has either 5 or 6 members. Whilst the rings may contain further heteroatoms selected from N, P, S or B, this is not preferred. Thus, apart from the potential heteroatoms represented by Y and Z, the A rings are preferably formed from carbon atoms. The A rings may contain double bonds and may be aromatic but preferably the rings contain no double bonds in addition to the double bond which must be present between the C and N in formula (I). Preferably, the rings are unsubstitued.

Thus suitable bicyclic groups include those illustrated below.

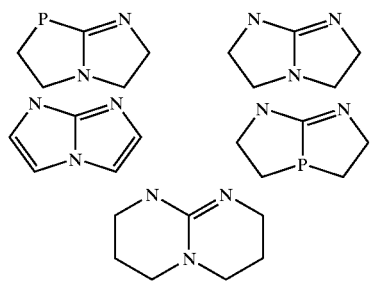

In a highly preferred embodiment the bicyclic group is formed from two fused six membered rings and Y and Z are nitrogen, i.e. the last or the five structures above.

The $\eta^5$-ligand may be any $\eta^5$-ligand which forms an η-bond with the complexing metal ion. Suitable ligands therefore include dipyridylmethanyl, indenyl, fluorenyl or cyclopentadienyl ligands. The $\eta^5$-ligand is substituted by groups $R_1$ and $(R")_m$ as hereinbefore defined. Hence, suitable procatalysts or use in the invention include those of formula

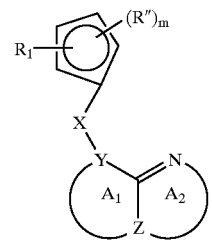

wherein $R_1$, R", m, X, Y, Z and rings $A_1$ and $A_2$ are as hereinbefore defined. Alternatively, the $\eta^5$-ligand is of formula

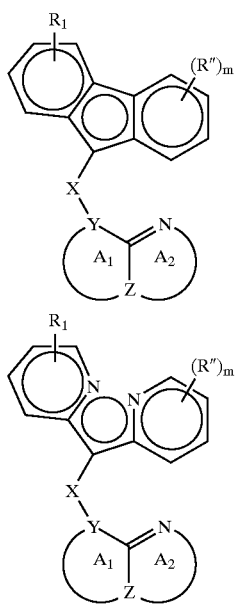

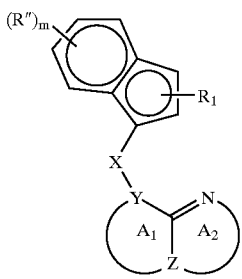

or

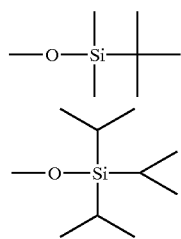

wherein $R_1$, R", m, X, Y, Z and rings $A_1$ and $A_2$ are as hereinbefore defined. In the above formula, the $R_1$ and R" groups may be bound to any ring of the $\eta^5$-ligand, i.e. although the $R_1$ group in the formula immediately above is depicted as being generally present on the 5-membered ring, the nomenclature is intended to cover the possibility or the $R_1$ group being present on the 6-membered ring.

The preferred nature of the groups $R_1$ and R" varies depending on the nature or the $\eta^5$-ligand. Where the $\eta^5$-ligand is a cyclopentadienyl, $R_1$ is preferably a group of formula OSiR'$_3$. Preferably R' is a $C_{1-12}$ hydrocarbyl group, e.g. a $C_{1-18}$ alkyl or alkenyl group, especially methyl or isopropyl.

Examples of suitable R'$_3$SiO groups in the compounds or procatalysts of the invention include and

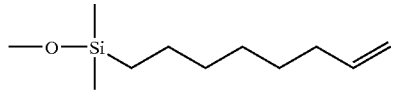

Where the $\eta^5$-ligand is a cyclopentadienyl group, the OSiR'$_3$ group may be situated at any position on the cyclopentadienyl ring but preferably is alpha to the carbon atom involved in bridging.

The cyclopentadienyl group itself may be substituted by up to three groups R" and R" preferably represents $C_{1-16}$ alkyl, especially methyl. In a highly preferred embodiment, three R" groups are present and R" is methyl. Since $R_1$ may also represent R" a cyclopentadienyl substituted by four methyl groups is also within the scope of the invention.

Also within the scope of the invention are cyclopentadienyl groups wherein one of the carbon atoms not bound to the bridging group X or if present the OSiR'$_3$ group, is replaced by a heteroatom selected from phosphorus, silicon, nitrogen or boron. It is stressed however, that preferably there are no heteroatoms present in the cyclopentadienyl ring.

Thus typical examples or suitable cyclopentadienyl type moieties include:

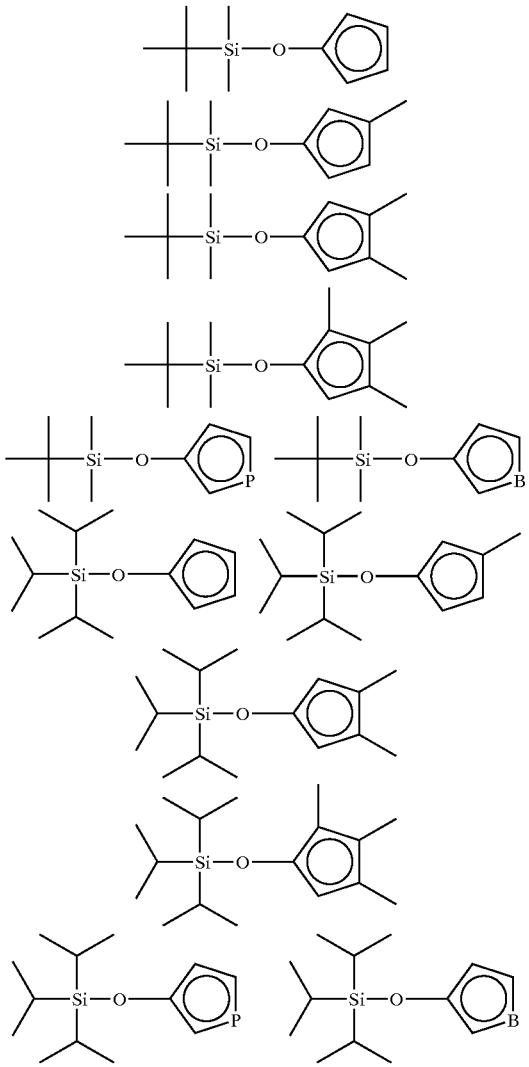

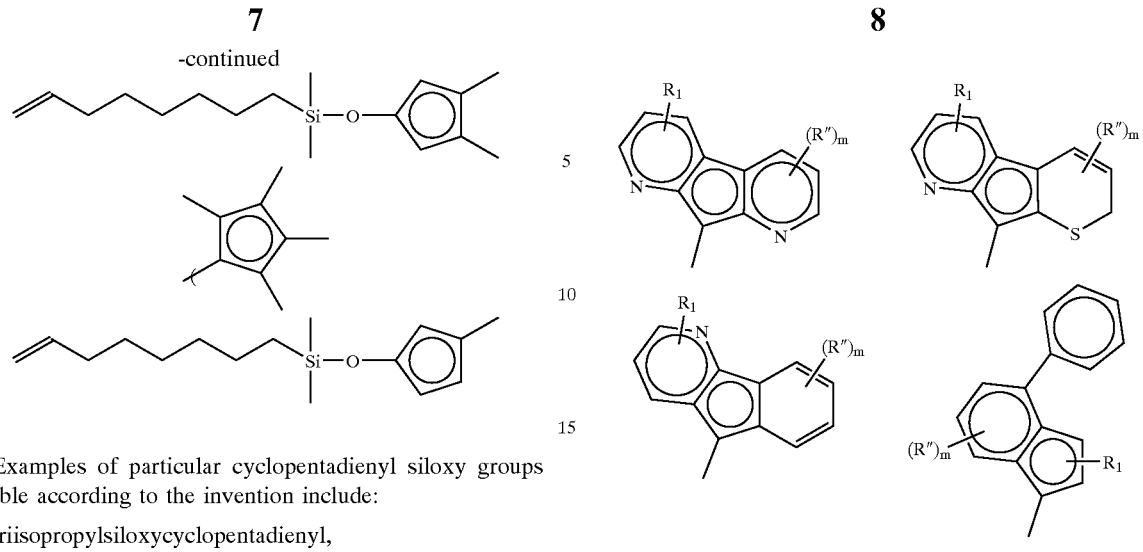

Examples of particular cyclopentadienyl siloxy groups usable according to the invention include:

triisopropylsiloxycyclopentadienyl, 1-triisopropylsiloxy-3-methyl-cyclopentadienyl, 1-triisopropylsiloxy-3,4-dimethyl-cyclopentadienyl, 1-triisopropylsiloxy-2,3,4-trimethyl-cyclopentadienyl, (dimethyltertbutylsiloxy)-cyclopentadienyl, 1-(dimethyltertbutylsiloxy)-3-methylcyclopentadienyl, 1-(dimethyltertbutylsiloxy)-3,4-dimethylcyclopentadienyl, 1-(dimethyltertbutylsiloxy)-2,3,4-trimethyl-cyclopentadienyl, 1-triisopropylsiloxy-2-phospholyl, 1-triisopropylsiloxy-3-phospholyl, 1-dimethyltertbutylsiloxy-2-phospholyl, 1-dimethyltertbutylsiloxy-3-phospholyl, 1-triisopropylsiloxy-2-borolyl, 1-triisopropylsiloxy-3-borolyl, 1-dimethyltertbutylsiloxy-2-borolyl, 1-dimethyltertbutylsiloxy-3-borolyl, 1-(dimethyloct-1-en-8-ylsiloxy)-3-methyl-cyclopentadienyl, 1-(dimethyloct-1-en-8-ylsiloxy)-3,4-dimethyl-cyclopentadienyl.

Where the $\eta^5$-ligand is a dipyridylmethanyl, indenyl or fluorenyl species the $R_1$ may also be a group of formula $OSiR'_3$ as hereinbefore described but preferably $R_1$ is hydrogen. R" may represent a $C_{1-6}$ alkyl, especially methyl but again in a preferred embodiment R" is hydrogen. Where the η ligand is indenyl, R" may preferably represent an n-alkenyl, e.g. n-hexyl.

Examples of particular further η-ligands are well known from the technical and patent literature relating to metallocene olefin polymerization catalysts, e.g. EP-A-35242 (BASF), EP-A-129368 (Exxon), EP-A-206794 (Exxon), PCT/FI97/00049 (Borealis), EP-A-318048, EP-A-643084, EP-A-69951, EP-A-410734, EP-A-128045, EP-B-35242 (BASF), EP-B-129368 (Exxon), WO97/23493, Organometallics 1995, 14, 471 and EP-B-206794 (Exxon). Further suitable η-ligands are those or formula

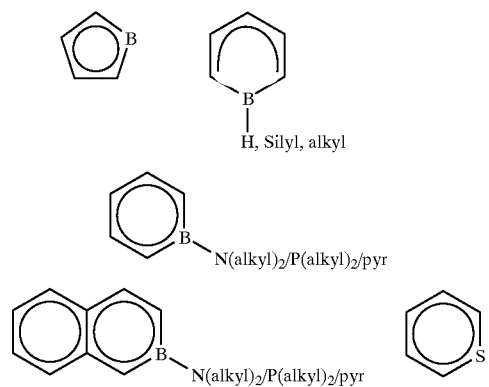

The bridging group X is preferably a one or two atom bridge comprising silicon or carbon. The bridge preferably connects to a carbon atom present in the 5-membered ring or the $\eta^5$-ligand. However, where the ligand comprises a heteroatom such as boron, the bridge may attach to the heteroatom or to the heteroatom's substituents. Where the bridge is formed from silicon, the bridge may be of formula —Si(R_2)_2 wherein each $R_2$ independently represents a $C_{1-10}$ alkyl, $C_{1-10}$ alkenyl, aryl, e.g. phenyl, trimethylsilyl, or both $R_2$ groups taken together may form a ring, e.g. five membered ring, with the Si. Where the bridge comprises carbon, the bridge is preferably a one atom bridge, e.g. —CH_2— or —CH(CH_3)_2—. Suitable bridges are depicted below

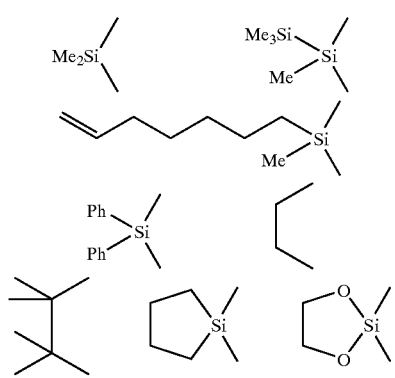

In a highly preferred embodiment, compound according to the invention is of formula
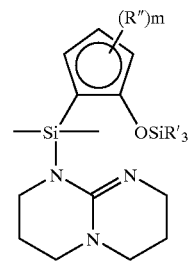
wherein R', m and R" are as hereinbefore described.
Further typical examples of the procatalysts or the invention include:
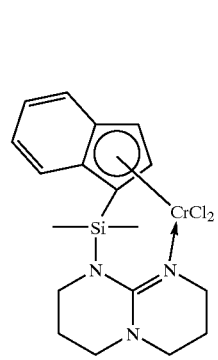
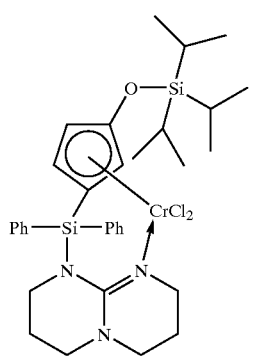
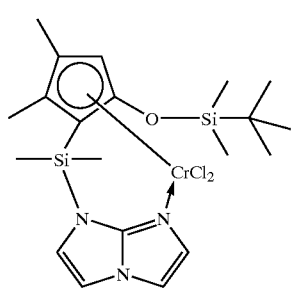
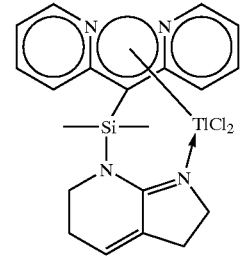
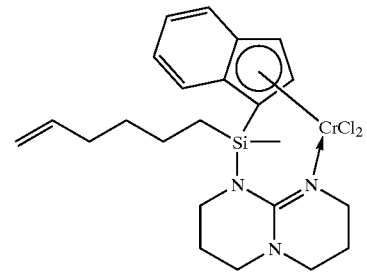
-continued
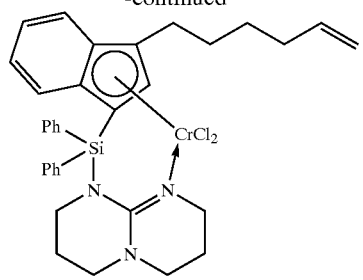
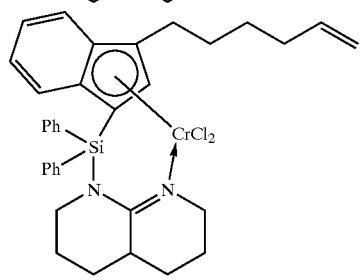
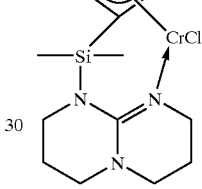
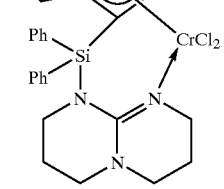
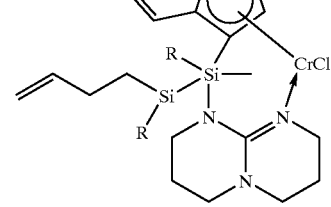
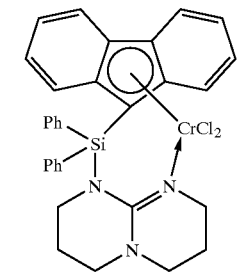
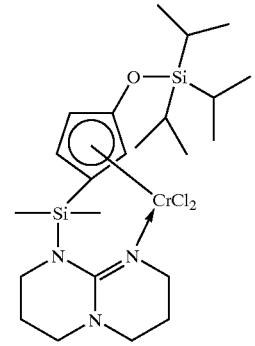
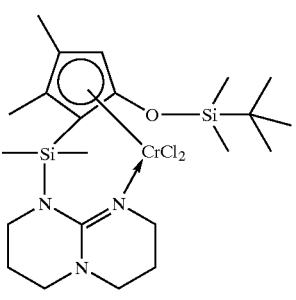
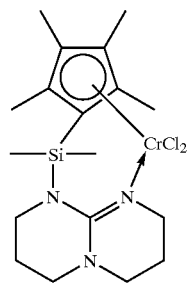

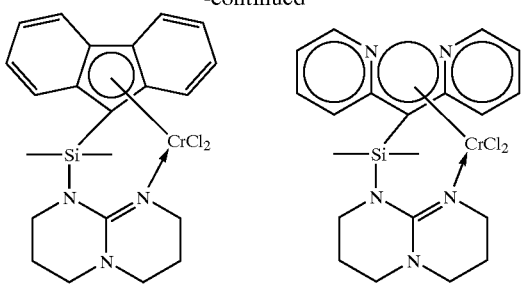

The procatalysts of the invention may be prepared by conventional techniques which will be readily devised by the person skilled in the art. Conveniently for example, the procatalyst is constructed by combining the bicyclic ligand with, for example, the siloxy cyclopentadienyl ligand followed by subsequent metallation. The bridging group may be carried by either the bicyclic ligand or the cyclopentadienyl ligand but conveniently the bridging group is attached to the bicyclic group first.

Where the bicyclic group is for example 1.5.7-triaza [4.4.0]bicyclo-dec-5-ene this may be deprotonated by a strong base and the resulting anion reacted with a bridging group such as dimethylsilyldichloride. The cyclopentadienyl η-ligands used according to the invention may be prepared by reaction of a corresponding siloxycyclopentadiene with an organolithium compound, eg methyllithium or butyllithium. The reaction or the lithium cyclopentadienyl species with the bicyclic ligand carrying bridiging group gives rise to a compound or the invention after further deprotonation. These reactions are depicted in the Scheme below.

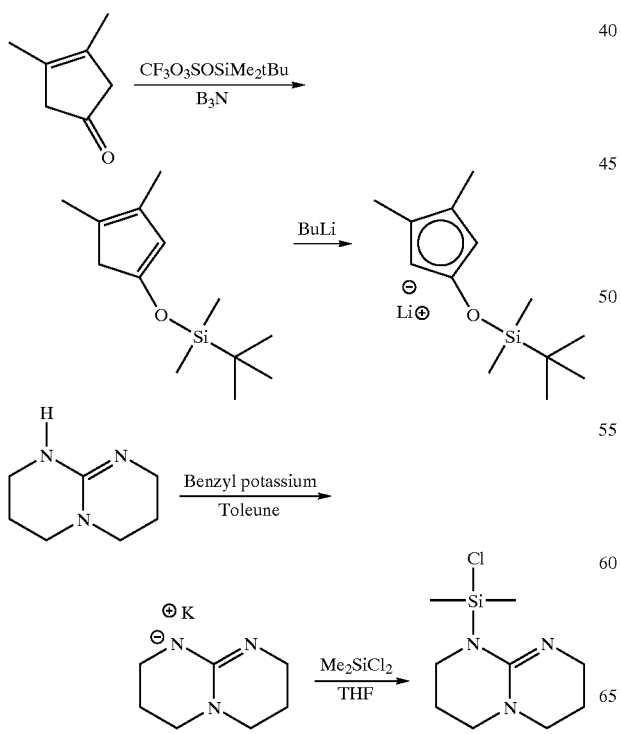

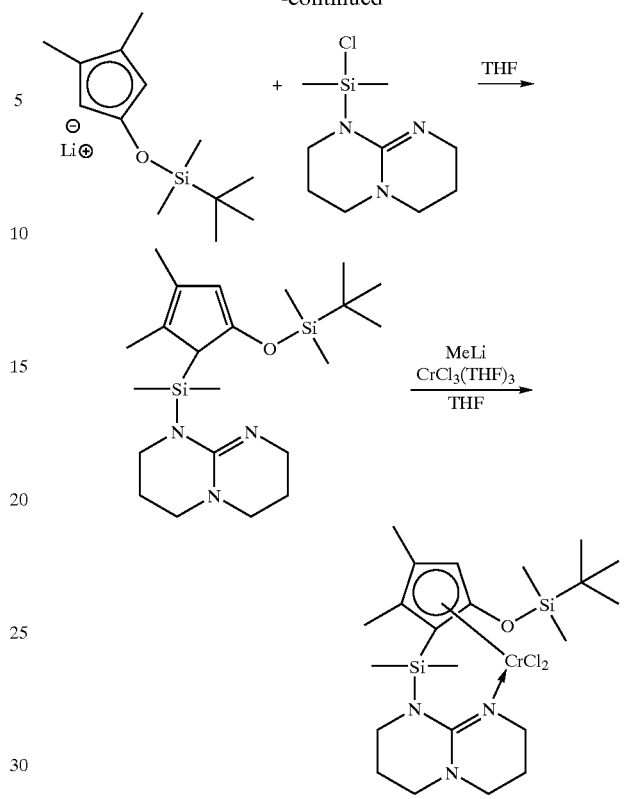

Fluorenyl and indenyl compounds of the invention may be prepared by analogous techniques to those required to prepare the cyclopentadienyl compounds.

Where the η-ligand is a dipyridylmethanediyl, the bicyclic nitrogen ligand may be reacted with a species generated as illustrated in the following scheme.

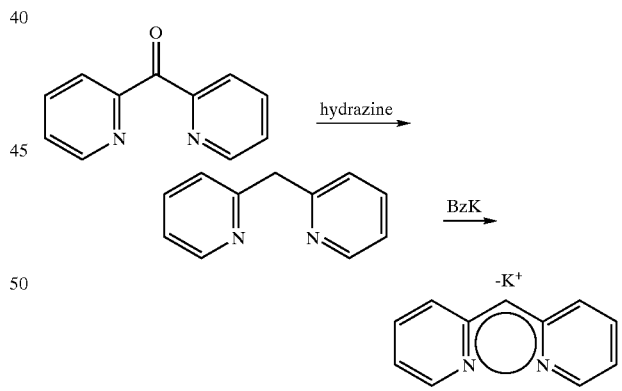

Deprotonation of the product again leaves the compound of the invention. The starting material may be functionalised as necessary to have required substituents using conventional synthetic chemistry. It is of course possible to have the dipyridylmethanediyl carry the bridging group using the following chemistry:

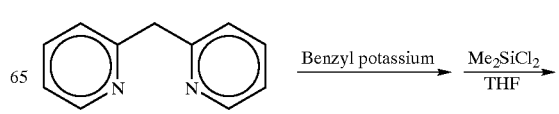

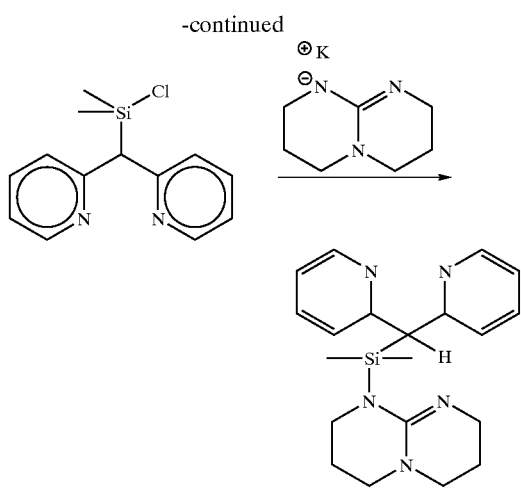

The compound can be metallated conventionally, eg by reaction with a halide or the metal M, preferably in an organic solvent, eg a hydrocarbon or a hydrocarbon/ether mixture.

σ-ligands other than chlorine may be introduced by displacement or chlorine from an η-ligand metal chloride by reaction with appropriate nucleophilic reagent (e.g. methyl lithium or methylmagnesium chloride) or using, instead or a metal halide, a reagent such as tetrakisdimethylamidotitanium or metal compounds with mixed chloro and dimethylamido ligands.

As mentioned above, the olefin polymerisation catalyst system of the invention comprises (i) a procatalyst formed from a metallated compound of formula (I) and (ii) an aluminium alkyl compound, or the reaction product thereof. While the aluminium alkyl compound may be an aluminium trialkyl (eg triethylaluminium (TEA)) or an aluminium dialkyl halide (eg diethyl aluminium chloride (DEAC)), it is preferably an alumoxane, particularly an alumoxane other than MAO, most preferably an isobutylalumoxane, eg TIBAO (tetraisobutylalumoxane) or HIBAO (hexaisobutylalumoxane). Alternatively however the alkylated (eg methylated) metallocene procatalysts of the invention (e.g. compounds or formula V wherein Z is alkyl) may be used with other cocatalysts, eg boron compounds such as $B(C_6F_5)_3$, $C_6H_5N(CH_3)_2H:B(C_6F_5)_4$, $(C_6H_5)_3C:B(C_6F_5)_4$ or Ni $(CN)_4[B(C_6F_5)_3]_4{}^{2-}$.

The metallocene procatalyst and cocatalyst may be introduced into the polymerization reactor separately or together or, more preferably they are pre-reacted and their reaction product is introduced into the polymerization reactor.

If desired the procatalyst, procatalyst/cocatalyst mixture or a procatalyst/cocatalyst reaction product may be used in unsupported form or it may be precipitated and used as such. However the metallocene procatalyst or its reaction product with the cocatalyst is preferably introduced into the polymerization reactor in supported form, eg impregnated into a porous particulate support.

The particulate support material used is preferably an organic or inorganic material, e.g. a polymer(such as for example polyethylene, polypropylene, an ethylene-propylene copolymer, another polyolefin or polystyrene or a combination thereof). Such polymeric supports may be formed by precipitating a polymer or by a prepolymerization, eg of monomers used in the polymerization for which the catalyst is intended. However, the support is especially preferably a metal or pseudo metal oxide such as silica, alumina or zirconia or a mixed oxide such as silica-alumina, in particular silica, alumina or silica-alumina. Particularly preferably, the support material is acidic, e.g. having an acidity greater than or equal to silica, more preferably greater than or equal to silica-alumina and even more preferably greater than or equal to alumina. The acidity of the support material can be studied and compared using the TPD (temperature programmed desorption or gas) method. Generally the gas used will be ammonia. The more acidic the support, the higher will be its capacity to adsorb ammonia gas. After being saturated with ammonia, the sample or support material is heated in a controlled fashion and the quantity of ammonia desorbed is measured as a function of temperature.

Especially preferably the support is a porous material so that the metallocene may be loaded into the pores of the support, e.g. using a process analogous to those described in WO94/14856 (Mobil), WO95/12622 (Borealis) and WO96/00243 (Exxon). The particle size is not critical but is preferably in the range 5 to 200 μm, more preferably 20 to 80 μm.

Before loading, the particulate support material is preferably calcined, ie heat treated, preferably under a non-reactive gas such as nitrogen. This treatment is preferably at a temperature in excess or 100° C., more preferably 200° C. or higher, e.g. 200–800° C., particularly about 300° C. The calcination treatment is preferably effected for several hours, e.g. 2 to 30 hours, more preferably about 10 hours.

The support may be treated with an alkylating agent before being loaded with the metallocene. Treatment with the alkylating agent may be effected using an alkylating agent in a gas or liquid phase, e.g. in an organic solvent for the alkylating agent. The alkylating agent may be any agent capable of introducing alkyl groups, preferably $C_{1-16}$ alkyl groups and most especially preferably methyl groups. Such agents are well known in the field of synthetic organic chemistry. Preferably the alkylating agent is an organometallic compound, especially an organoaluminium compound (such as trimethylaluminium (TMA), dimethyl aluminium chloride, triethylaluminium) or a compound such as methyl lithium, dimethyl magnesium, triethylboron, etc.

The quantity of alkylating agent used will depend upon the number of active sites on the surface of the carrier. Thus for example, for a silica support, surface hydroxyls are capable of reacting with the alkylating agent. In general, an excess of alkylating agent is preferably used with any unreacted alkylating agent subsequently being washed away.

Where an organoaluminium alkylating agent is used, this is preferably used in a quantity sufficient to provide a loading of at least 0.1 mmol Al/g carrier, especially at least 0.5 mmol Al/g, more especially at least 0.7 mmol Al/g, more preferably at least 1.4 mmol Al/g carrier, and still more preferably 2 to 3 mmol Al/g carrier. Where the surface area of the carrier is particularly high, lower aluminium loadings may be used. Thus for example particularly preferred aluminium loadings with a surface area of 300–400 m²/g carrier may range from 0.5 to 3 mmol Al/g carrier while at surface areas of 700–800 m²/g carrier the particularly preferred range will be lower.

Following treatment of the support material with the alkylating agent, the support is preferably removed from the treatment fluid and any excess treatment fluid is allowed to drain off.

The optionally alkylated support material is loaded with the procatalyst, preferably using a solution of the procatalyst in an organic solvent therefor, e.g. as described in the patent publications referred to above. Preferably, the volume of procatalyst solution used is from 50 to 500% or the pore volume of the carrier, more especially preferably 80 to 120%. The concentration of procatalyst compound in the solution used can vary from dilute to saturated depending on the amount of metallocene active sites that it is desired be loaded into the carrier pores.

The active metal (ie. the metal or the procatalyst) is preferably loaded onto the support material at from 0.1 to 4%, preferably 0.5 to 3.0%, especially 1.0 to 2.0%, by weight metal relative to the dry weight of the support material.

After loading of the procatalyst onto the support material, the loaded support may be recovered for use in olefin polymerization, e.g. by separation of any excess procatalyst solution and if desired drying or the loaded support, optionally at elevated temperatures, e.g. 25 to 80° C.

Alternatively, a cocatalyst, e.g. an alumoxane or an ionic catalyst activator (such as a boron or aluminium compound, especially a fluoroborate) may also be mixed with or loaded onto the catalyst support material. This may be done subsequently or more preferably simultaneously to loading of the procatalyst, for example by including the cocatalyst in the solution of the procatalyst or, by contacting the procatalyst loaded support material with a solution of the cocatalyst or catalyst activator, e.g. a solution in an organic solvent. Alternatively however any such further material may be added to the procatalyst loaded support material in the polymerization reactor or shortly before dosing of the catalyst material into the reactor.

In this regard, as an alternative to an alumoxane it may be preferred to use a fluoroborate catalyst activator, especially a $B(C_6F_5)_3$ or more especially a $^\ominus B(C_6F_5)_4$ compound, such as $C_6H_5N(CH_3)_2H:B(C_6F_5)_4$ or $(C_6H_5)_3C:B(C_6F_5)_4$. Other borates or general formula $(cation^+)_a (borate^-)_b$ where a and b are positive numbers, may also be used.

Where such a cocatalyst or catalyst activator is used, it is preferably used in a mole ratio to the metallocene of from 0.1:1 to 10000:1, especially 1:1 to 50:1, particularly 1:2 to 30:1. More particularly, where an alumoxane cocatalyst is used, then for an unsupported catalyst the aluminium:metallocene metal (M) molar ratio is conveniently 2:1 to 10000:1, preferably 50:1 to 1000:1. Where the catalyst is supported the Al:M molar ratio is conveniently 2:1 to 10000:1 preferably 50:1 to 400:1. Where a borane cocatalyst (catalyst activator) is used, the B:M molar ratio is conveniently 2:1 to 1:2, preferably 9:10 to 10:9, especially 1:1. When a neutral triarylboron type cocatalyst is used the B:M molar ratio is typically 1:2 to 500:1, however some aluminium alkyl would normally also be used. When using ionic tetraaryl borate compounds, it is preferred to use carbonium rather than ammonium counterions or to use B:M molar ratio below 1:1.

Where the further material is loaded onto the procatalyst loaded support material, the support may be recovered and if desired dried before use in olefin polymerization.

The olefin polymerized in the method or the invention is preferably ethylene or an alpha-olefin or a mixture or ethylene and an α-olefin or a mixture of alpha olefins, for example $C_{2-20}$ olefins, e.g. ethylene, propene, n-but-l-ene, n-hex-l-ene, 4-methyl-pent-l-ene, n-oct-l-ene-etc. The olefins polymerized in the method of the invention may include any compound which includes unsaturated polymerizable groups. Thus for example unsaturated compounds, such as $C_{6-20}$ olefins (including cyclic and polycyclic olefins (e.g. norbornene)), and polyenes, especially $C_{6-20}$ dienes, may be included in a comonomer mixture with lower olefins, e.g. $C_{2-5}$ α-olefins. Diolefins (ie. dienes) are suitably used for introducing long chain branching into the resultant polymer.

Examples of such dienes include α,ω linear dienes such as 1,5-hexadiene, 1,6-heptadiene, 1,8-nonadiene, 1,9-decadiene, etc.

In general, where the polymer being produced is a homopolymer it will preferably be polyethylene or polypropylene. Where the polymer being produced is a copolymer it will likewise preferably be an ethylene or propylene copolymer with ethylene or propylene making up the major proportion (by number and more preferably by weight) or the monomer residues. Comonomers, such as $C_{4-6}$ alkenes, will generally be incorporated to contribute to the mechanical strength or the polymer product.

Usually metallocene catalysts yield relatively narrow molecular weight distribution polymers; however, if desired, the nature or the monomer/monomer mixture and the polymerization conditions may be changed during the polymerization process so as to produce a broad bimodal or multimodal molecular weight distribution (MWD) in the final polymer product. In such a broad MWD product, the higher molecular weight component contributes to the strength or the end product while the lower molecular weight component contributes to the processability of the product, e.g. enabling the product to be used in extrusion and blow moulding processes, for example for the preparation of tubes, pipes, containers, etc.

A multimodal MWD can be produced using a catalyst material with two or more different types of active polymerization sites, e.g. with one such site provided by the metallocene on the support and further sites being provided by further catalysts, e.g. Ziegler catalysts, other metallocenes, etc. included in the catalyst material.

Polymerization in the method of the invention may be effected in one or more, e.g. 1, 2 or 3, polymerization reactors, using conventional polymerization techniques, e.g. gas phase, solution phase, slurry or bulk polymerization.

In general, a combination of slurry (or bulk) and at least one gas phase reactor is often preferred, particularly with the reactor order being slurry (or bulk) then one or more gas phase.

For slurry reactors, the reaction temperature will generally be in the range 60 to 110° C. (e.g. 85–110° C.), the reactor pressure will generally be in the range 5 to 80 bar (e.g. 50–65 bar), and the residence time will generally be in the range 0.3 to 5 hours (e.g. 0.5 to 2 hours). The diluent used will generally be an aliphatic hydrocarbon having a boiling point in the range −70 to +100° C. In such reactors, polymerization may if desired be effected under supercritical conditions.

For gas phase reactors, the reaction temperature used will generally be in the range 60 to 115° C. (e.g. 70 to 110° C.), the reactor pressure will generally be in the range 10 to 25 bar, and the residence time will generally be 1 to 8 hours. The gas used will commonly be a non-reactive gas such as nitrogen together with monomer(e.g. ethylene).

For solution phase reactors, the reaction temperature used will generally be in the range 130 to 270° C., the reactor pressure will generally be in the range 20 to 400 bar and the residence time will generally be in the range 0.1 to 1 hour. The solvent used will commonly be a hydrocarbon with a boiling point in the range 80–200° C.

Generally the quantity of catalyst used will depend upon the nature or the catalyst, the reactor types and conditions and the properties desired for the polymer product. Conventional catalyst quantities, such as described in the publications referred to herein, may be used.

All publications referred to herein are hereby incorporated by reference.

EXPERIMENTAL

General Considerations

All operations were carried out in argon or nitrogen atmosphere using standard Schlenk, vacuum and dry box techniques. Solvents were dried with potassium benzophenone ketyl and distilled under argon prior to use. 1.5.7-triaza[4.4.0]bicyclo-dec-5-ene (TAB-H) (Fluka) and dipyridylketone (DPM-H) (Fluka) were used as purchased. Benzyl potassium was prepared according to Schlosser, M. and Hartmann, J. Angew. Chem 1973, 85, 544–545. $CrCl_3$(THF)$_3$ and $TiCl_3$(THF)$_3$ were prepared according to W. A. Herrmann and G. Brauer, Synthetic Methods or Organometallic and Inorganic Chemistry, Vol. 1: Literature, Laboratory Techniques and Common Starting Materials, Thieme 1996. 1H- and 13C-NMR spectra were recorded using JEOL JNM-EX 270 MHz FT NMR spectrometer with tetramethylsilane (TMS) as an internal reference. 13C-CPMAS NMR and the mass spectra were recorded at Fortum Oil and Gas Oy, Analytical Research department. The CPMAS-NMR spectra were recorded using Chemagnetics Infinity 270 MHz equipment and the direct inlet MS spectra were produced by VG TRIO 2 quadrupole mass spectrometer in electron impact ionisation mode (EIMS) (70 eV). The GC-MS analyses were performed using Hewlett Packard 6890/5973 Mass Selective Detector in electron impact ionisation mode (70 eV) equipped with a silica capillary column (30 m×0.25 mm i.d.). The FTIR spectra were recorded at Borealis Analytical Research department using Perkin-Elmer Spectrum 2000 spectrometer with inert diamond ATR accessory and 4 cm-1 resolution. Thermogravic measurements (TG) were recorded using GWB METTLER TG50 Termobalance and the Differential Scanning Calorimetry (DSC) and melting point analyses using GWB METTLER DSC-30 under inert conditions at Borealis Analytical Research department. The polymerization tests were carried out using MAO, 30% solution in toluene purhased from Albermarle. Test polymerizations were carried out in pentane at 60° C. and at 80° C. with hydrogen present using an Al/M ratio or 1000 unless otherwise stated. A Büchi 2 L stirred reactor with mantle heating was used for the polymerization tests.

EXAMPLE 1

Synthesis of (1.5.7-triaz[4.4.0]bicyclo-dec-5-enyl) potassium, $C_7H_{12}KN_3$

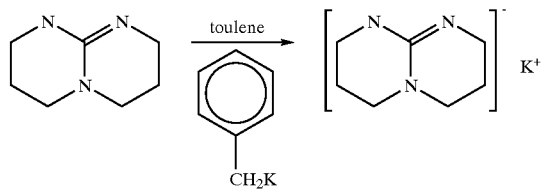

Red solid benzyl potassium (9.6 g, 73.3 mmol) was added into the solution of 1.5.7-triaza[4.4.0]bicyclo-dec-5-ene (10.2 g, 73.3 mmol) in 350 ml of dry toluene at −40° C. The temperature was allowed to warm to room temperature and the mixture stirred for 16 hours. The colour changed via red to a white slurry. The solvents were removed in a vacuum, the product washed with 3×60 ml of ether and dried in a vacuum to obtain 10.1 g (78%) of white powder. $^1$H-NMR in THF-$d_8$; δ: 3.17 (t, 4H); 2.98 (t, 4H); 1.69 (t, 4H). The potassium salt product could not be analysed with MS. Elemental analysis calc.: C 47.4%, H 6.8%, N 23.7%, K 22.1%. Elemental analysis found: C 46.0%, H 6.4%, N 23.1%.

EXAMPLE 2

Synthesis of triazabicyclodec-ene-yl-1-dimethylsilylchloride $C_9H_{18}ClN_3Si$.

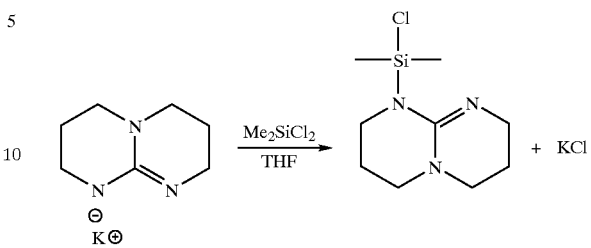

1.5.7-triaza[4.4.0]bicyclo-dec-5-enyl potassium 13.0 g (73.1 mmol) dissolved in 200 mL of THF was added into a solution of 55 mL (438.6 mmol) of $Me_2SiCl_2$ in 50 mL THF over 3 hours at ambient temperature. Colour changed from yellow to dark yellow. The solution was stirred for 2 hours at ambient temperature after which the mixture containing a gelish precipitate of KCl was filtrated and washed with 2×30 mL of THF. Solvent was removed under vacuum to obtain an off yellow solid which was extracted with 3×30 mL of pentane and and filtrated. The product was purified by recrystallization and filtration from cold (−30° C.) pentane yielding colorless, needle-like crystals. Yield 12.9 g (76.4%). $^1$H-NMR CDCl$_3$ δ: 3.16 (t, 4H), 3.11 (t, 4H), 1.88 (t, 4H), 0.46 (s, 6H). $^{13}$C-NMR CDCl$_3$δ: 154.9, 45.3, 38.6, 23.3, 7.9. EIMS analysis showed the decomposition pattern of the parent ion of the title compound $C_9H_{18}ClN_3Si$ $M^+$=231.80 g mol$^{-1}$. Elemental analysis calc. C 46.63%, H 7.83%, N 18.13%, Cl 15.29%, Si 12.12%; Found. C 46.52%, H 7.80%, N 18.24%, Cl 15.15%, Si 12.05%.

EXAMPLE 3 t-Butyldimethylsiloxy-3,4-dimethylcyclopentadienyl lithium

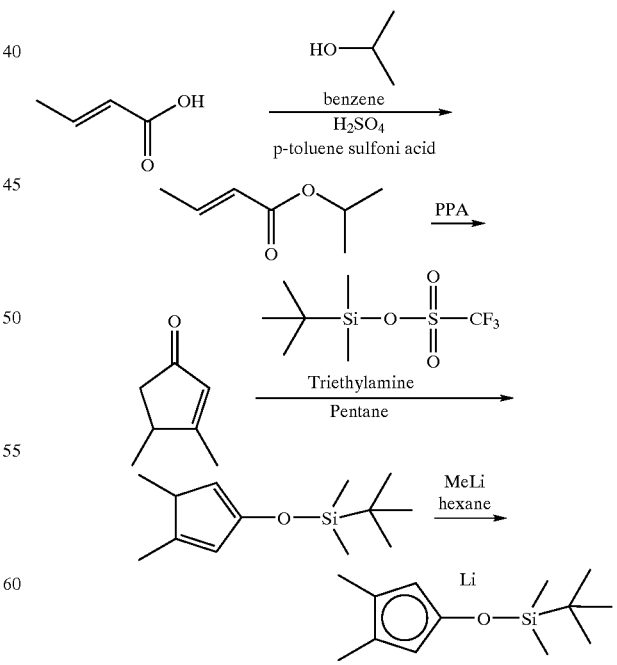

40.0 g (465 mmol) of crotonic acid (Fluka 28010), 25.1 g (418 mmol) of isopropanol (Merck 1.09634.2500), 200 mL of benzene, 4.2 g of conc. $H_2SO_4$ and 2.1 g of para-toluene sulfonic acid was charged to a 500 mL flask equipped with a magnetic stirrer bar and Dean-Stark water separator. The mixture was refluxed until water formation ceased. 200 mL of ether was added to the mixture, and then washed with several portions of NaHCO$_3$ (aq., sat.) until the the acid was neutralized. Organic phase was separated, dried with MgSO$_4$ and filtered. Solvent was removed under reduced pressure and the remainder distilled at 95° C. to give 30.5 g of isopropylcrotonate. Yield 57%. $^1$H-NMR (CDCl$_3$): 6.95 (dq, 1H), 5.82 (d, 1H), 5.05 (sept, 1H), 1.88 (d, 3H), 1.25 (d, 6H).

811 g of polyphosphoric acid (Fluka 81340) was loaded to a round bottom flask equipped with a reflux condenser and a magnetic stirrer bar and heated to 100° C. 104 g (810 mmol) of isopropylcrotonate was added to the flask and the mixture was stirred for 2 hours at 100° C. The resulted mixture was poured to >>1,5 kg of crushed ice. At room temperature the mixture was saturated with NH$_4$Cl and extracted with 4×100 mL of ether. The combined ether fractions were dried over MgSO$_4$ and filtered. Solvent was removed under reduced pressure and the remainder distilled (0.2 mbar, 33° C., bath 90° C.) to give 47.99 g of 3,4-dimethylcyclopentenone. Yield 54%. $^1$H-NMR (CDCl$_3$): 5.86 (s, 1H), 2.80 (m, 1H), 2.64 (dd, 1H), 2.07 (s, 3H), 2.00 (dd, 1H), 1.18 (d, 3H).

12.23 g (111.0 mmol) of 3,4-dimethylcyclopentenone, 11.31 g (111.8 mmol) of triethylamine dried with molecular sieves and 300 mL of dry pentane were mixed at room temperature. During 13 minutes 29.44 g (111.4 mmol) of t-butyldimethylsilyltrifluoromethylsulfonate (Fluka 97742) was added to the mixture. After stirring for 2.5 hour the supernatant pentane fraction was separated, solvent removed under reduced pressure and the remainder distilled (0.03 mbar, 34–40° C., bath 100° C.) resulting in 19.74 g of isomer isomer mixture of t-butyldimethylsiloxy-3,4-dimethylcyclopentadienes. Yield 79%. $^1$H-NMR spectrum was complicated due to presence of at least 3 isomers. The product was characterised by GC/MS technique, which showed presence of three components (GC) each showing M+ peak at 224 (MS).

10 g (44.6 mmol) of isomer mixture of t-butyldimethylsiloxy-3,4-dimethylcyclopentadienes was mixed with 200 mL of pentane at room temperature. At −20° C. 28.4 mL (44.6 mmol) of 1.57 M t-butyllithium solution in hexanes (Acros 18128-0900) was added. Temperature was increased to 20° C. during 15 hours while stirring. The resulted solid product was separated by filtration and washed with 2×100 mL of pentane. Remaining solvent was removed under reduced pressure. 7.07 g of t-butyl-dimethylsiloxy-3,4-dimethylcyclopentadienyl lithium was isolated. Yield 69%. $^1$H-NMR (THF-d$_8$): 4.88 (s, 2H), 1.95 (s, 6H), 0.95 (s, 9H), 0.08 (s, 6H).

EXAMPLE 4
Synthesis of Tri-isopropylsiloxycyclopentadienyl Lithium

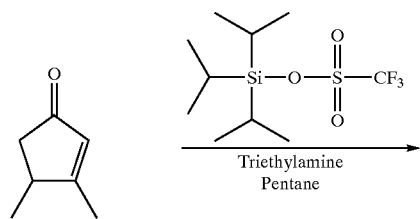

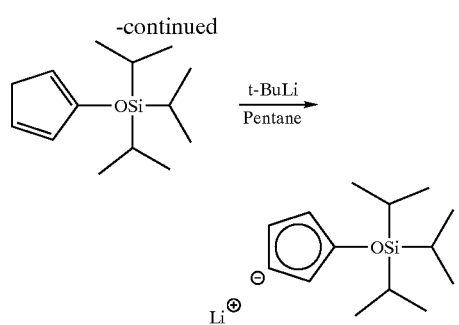

Triisopropylsiloxycyclopentadiene was prepared analogously to example 3 using triisopropylsilyl-trifluoromethylsulfonate (Fluka 91746) and cyclopent-2-enone (Fluka 29827) as starting materials. It was not isolated but lithiated immediately to avoid spontaneous Diels-Alder dimerisation of the product. Lithiation was performed analogously to example 3 and afforded triisopropylsiloxycyclopentadienyl lithium in 81% yield. $^1$H-NMR (THF-d$_8$): 5.22 (m, 2H), 5.17 (m, 2H), 1.11 (m, 3H), 1.04 (d, 18H).

EXAMPLE 5
Synthesis of Triazabicyclodec-ene-yl-1-dimethylsilyl-dimethyl-tertbutylsiloxy Dimethylcyclopentadiene (mixture of isomers) C$_{22}$H$_{41}$N$_3$OSi$_2$

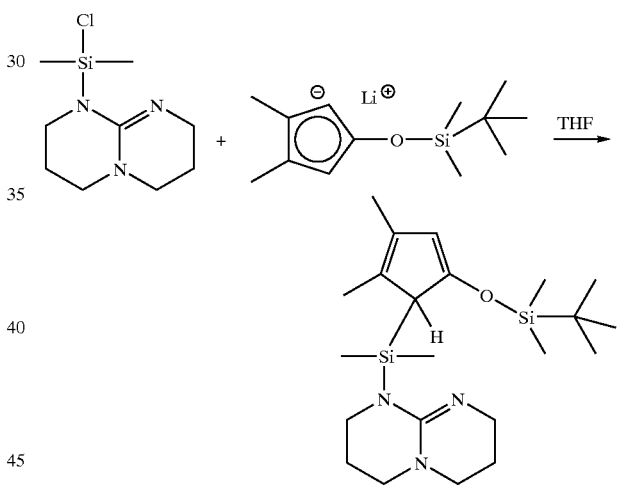

1.2 g (5.21 mmol) of t-butyldimethylsiloxy-3,4-dimethylcyclopentadienyl lithium dissolved in 100 mL of THF was added over 1 h into a solution of 1.2 g (5.21 mmol) of triazabicyclodec-ene-yl-1-dimethylsilylchloride in 50 mL of THF at −70° C. to give an orange transparent solution. The solution was refluxed for 16 hours after which the solvent was removed under vacuum. The product was extracted into pentane, filtrated and cooled to −30° C. for 16 hours. Trace insolubilities were filtrated off at −30° C. and the solvent removed under vacuum to give 98% pure, brown oily mixture of double bond and stereoisomers. Yield 1.6 g (73.3%). The EIMS analysis showed the decomposition pattern of the parent ion of the title compound C$_{22}$H$_{41}$N$_3$OSi$_2$ M$^+$=419.76 g mol$^{-1}$, fragmentation peaks at 404, 270, 224 and 196. $^1$H-NMR of the major isomer in THF-d$_8$ δ: 5.02 (s, 1H) 3.41 (s, 1H) 3.18 (m, 4H) 3.06 (m, 4H) 2.02 (s, 3H) 1.95 (s, 3H) 1.78 (m, 4H) 0.97 (s, 9H) 0.24 (s, 3H), 0.22 (s, 3H), 0.19 (s, 3H), 0.10 (s, 3H). $^{13}$C-NMR THF-d$_8$ δ: 160.9, 151.6, 131.7, 124.6, 110.6, 95.5, 53.0, 48.9, 43.3, 27.0, 26.4, 24.7, 13.0, 0.9, −4.1, −4.6.

EXAMPLE 6

Synthesis of triazabicyclodec-ene-yl-1-dimethylsilyl-dimethyl-tertbutylsiloxy dimethylcyclopentadienyl chromium dichloride $C_{22}H_{40}Cl_2CrN_3OSi_2$

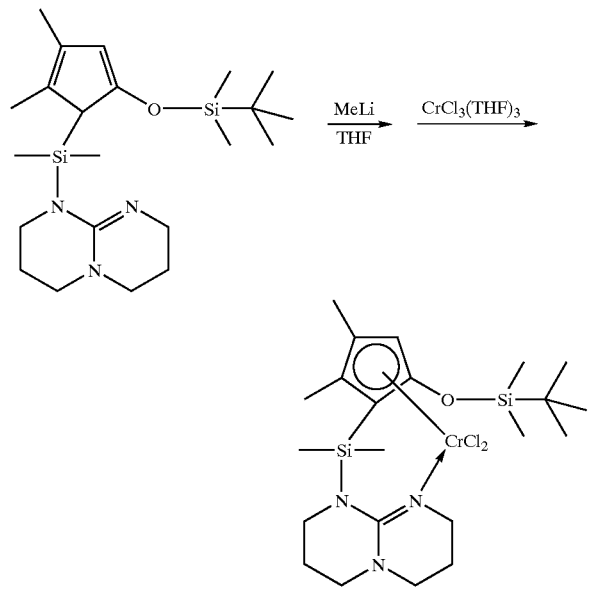

1.8 mL of MeLi (1.6 M solution in diethyl ether, 3.34 mmol) was added into a solution of 1.6 g (3.34 mmol) of triazabicyclodec-ene-yl-1-dimethylsilyl-dimethyl-tertbutylsiloxy dimethylcyclopentadiene in 50 mL THF at +50° C. over 5 minutes and stirred at ambient temperature for 16 hours. $CrCl_3(THF)_3$ (3.34 mmol) dissolved in THF was added over 40 minutes at −50° C. to give a dark blue solution which was stirred at ambient temperature for 16 hours. Solvents were removed under vacuum and the product extracted in toluene, filtered and evaporated. The raw product was purified by washing with cold pentane. Yield 1.0 g (52.2%) of dark blue microcrystalline solid. The compound was paramagnetic, NMR identification was not possible. The EIMS analysis showed the decomposition pattern of the parent ion of the title compound $C_{22}H_{40}Cl_2CrN_3OSi_2$ M+=541.65 g mol−1, fragmentation peaks at 504, 468, 418, 287, 224, 196 and 138. Melting point: 145° C. (broad peak in DSC). TG analysis (from 30° C. to 891° C., 10° C./min) showed 57.7% loss of weight in a one phase process at 286° C. averaged delta temperature. Crystals suitable for X-ray analysis were not obtained because of the presence of the two stereoisomers (rac and meso type) which resulted in the precipitation of microcrystalline solid. Elemental analysis calc. C 48.78%, H 7.44%, N 7.76%, Cl 13.09%, Si 10.37%, Cr 9.60%; Found C 49.02%, H 7.56%, N 7.94%, Cl 12.91%, Si 10.11%, Cr 9.44%.

EXAMPLE 7

Synthesis of Triazabicyclodec-ene-yl-1-dimethylsilyl-tri-isopropylsiloxy Cyclopentadiene (Mixture of Isomers) $C_{23}H_{43}N_3OSi_2$

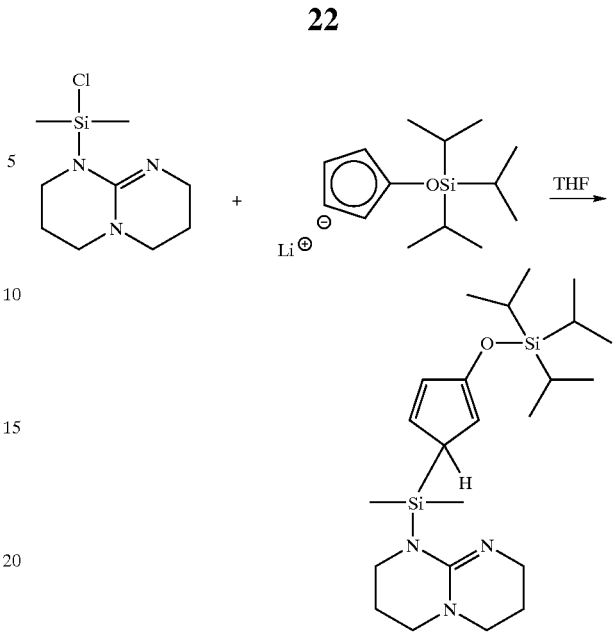

3.2 g (12.3 mmol, 92.6%) of tri-isopropylsiloxy-cyclopentadienyl lithium dissolved in 70 mL of THF was added over 40 minutes into a solution of 2.8 g (12.3 mmol) of triazabicyclodec-ene-yl-1-dimethylsilylchloride in 70 mL of THF at −70° C. to give a red mixture. The mixture was refluxed for 16 hours after which the solvent was removed under vacuum. The product was extracted into pentane, filtrated and the filtrate cooled to −30° C. for 16 hours after which the insolubles were filtered off at −30° C. The filtrate was then cooled to −70° C. for 6 h and the trace insolubles filtrated off at −70° C. The pentane was then removed under vacuum to give a dark brown, viscous oily mixture of double bond and regioisomers. Yield 3.1 g (57.6%). The EIMS analysis showed the decomposition pattern of the parent ion of the title compound $C_{23}H_{43}N_3OSi_2$ M+=433.78 g mol−1, fragmentation peaks at 418, 390, 238 and 196. $^1$H-NMR major isomer in THF-$d_8$ δ: 6.39 (m, 1H) 6.21 (m, 1H) 5.62 (m, 1H) 3.19 (m, 4H) 3.08 (m, 4H) 2.92 (m, 1H) 1.80 (m, 4H) 1.20 (m, 3H) 1.18 (s, 18H) 0.25 (s, 6H). $^{13}$C-NMR major isomer (1,3-substituted regioisomer) in THF-$d_8$ δ: 149.0, 131.8, 130.8, 130.0, 105.0, 102.0, 47.0, 41.2, 22.7, 16.2, 11.2, 0.4. The compound decomposed during the elemental analysis sample preparation.

EXAMPLE 8

Synthesis of triazabicyclodec-ene-yl-1-dimethylsilyl-tri-isopropylsiloxy cyclopentadienyl chromium dichloride (Mixture of Isomers) $C_{23}H_{42}N_3Cl_2CrOSi_2$

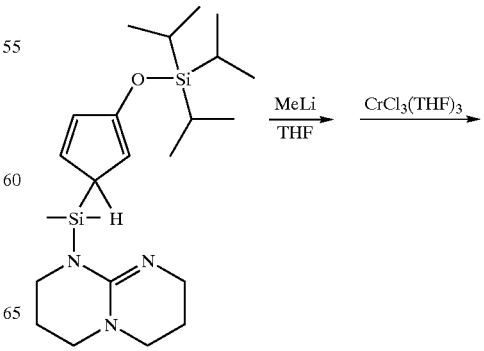

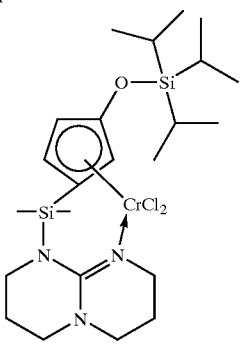

3.7 mL of MeLi (1.9 M solution in diethyl ether, 7.04 mmol) was added into a solution of 3.1 g (7.04 mmol) of triazabicyclodec-ene-yl-1-dimethylsilyl-tri-isopropylsiloxy-cyclopentadiene in 70 mL THF at +50° C. over 5 minutes and stirred at ambient temperature for 16 hours. $CrCl_3$ $(THF)_3$ (7.04 mmol) dissolved in 50 mL THF was added over 30 minutes at −30° C. to give a dark blue-green solution which was stirred at ambient temperature for 16 hours. Solvents were removed under vacuum and the product extracted in toluene, filtered and evaporated. The raw product was purified by washing with cold pentane. Yield 1.9 g (48.6%) of blue-green microcrystalline solid. The compound was paramagnetic, NMR identification was not possible. The EIMS analysis showed the decomposition pattern of the parent ion of the title compound $C_{23}H_{42}Cl_2CrN_3OSi_2$ $M^+=555.68$ g mold$^{-1}$, fragmentation peaks at 499, 477, 238, 192 and 178. Melting point: 170.9° C. (broad peak in DSC). TG analysis (from 30° C. to 891° C., 10° C./min) showed 55.2% loss of weight in a two phase process at 242° C. averaged delta temperature. Mp 170.9° C. Crystals suitable for X-ray analysis were not obtained because of the presence or the two stereoisomers (rac and meso type) which resulted in the precipitation of microcrystalline solid. Elemental analysis calc. C 49.71%, H 7.62%, N 7.56%, Cl 12.76%, Cr 9.36%, O 2.88%, Si 10.11%; Found C 49.50%, H 7.65%, N 7.31%, Cl 12.93%, Si 9.98%, Cr 9.48%.

EXAMPLE 9
Synthesis of Triazabicyclodec-ene-yl-1-dimethylsilyl-fluorene $C_{22}H_{27}N_3Si$

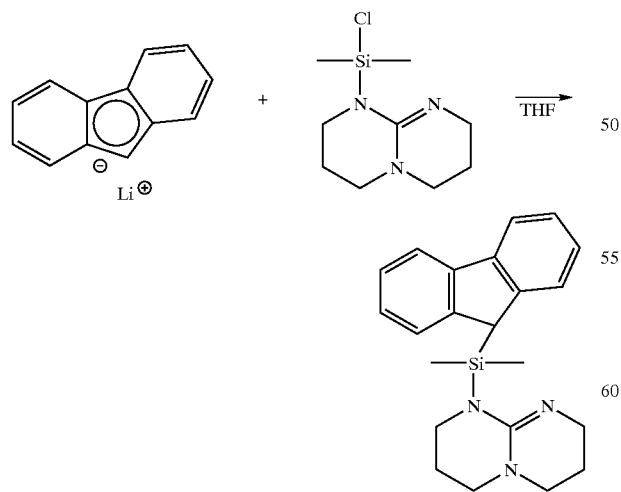

Fluorenyllithium (prepared from fluorene via treatment of butyllithium) 0.7 g (4.08 mmol) dissolved in 50 mL of THF was added over 30 minutes into a solution of 0.9 g (4.08 mmol) of triazabicyclodec-ene-yl-1-dimethyl-silylchloride in 50 mL of THF at −70° C. The yellowish solution was stirred at ambient temperature for 16 hours after which the solvent was removed under vacuum. The product was extracted into pentane, filtrated and cooled to −30° C. for 16 hours. The product precipitated as yellowish transparent crystals which were filtrated and dried in a vacuum. Yield 1.1 g (73.8%). The EIMS analysis showed the decomposition pattern of the parent ion of the title compound $C_{22}H_{41}N_3OSi_2$ $M^+=361.56$ g mol$^{-1}$, fragmentation peaks at 346, 196, 165 and 138. $^1$H-NMR in $CDCl_3$ δ: 7.90 (d, 2H), 7.58 (d, 2H), 7.38 (dd 2H) 7.30 (dd, 2H), 4.95 (s, 1H) 3.22 (t, 4H) 3.19 (t, 4H) 1.91 (q, 4H) −0.1 (s, 6H). $^{13}$C-NMR in $CDCl_3$ δ: 161.3, 146.3, 140.7, 125.7, 124.7, 124.3, 119.5, 48.3, 43.2, 42.7, 23.8, −2.5.

EXAMPLE 10

Synthesis of triazabicyclodec-ene-yl-1-dimethylsilyl-fluorenyl chromium dichloride $C_{22}H_{26}Cl_2CrN_3Si$ (Descriptive Example)

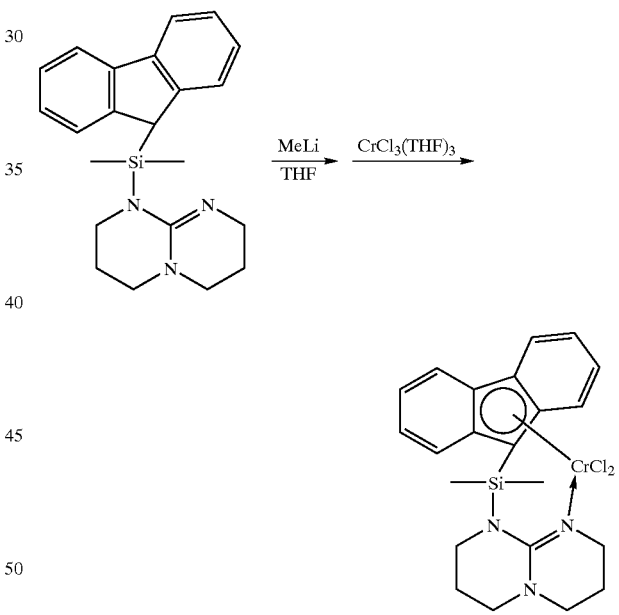

1.7 mL of methyl lithium (2.94 mmol, 1.76 M solution in diethyl ether) was added at −30° C. into a solution of triazabicyclodec-ene-yl-1-dimethylsilyl-fluorene 1.1 g (2.94 mmol) in 50 mL of THF. The solution became bright neon yellow and yellowish precipitate formed. The mixture was stirred at ambient temperature for 16 hours. Then $CrCl_3$ $(THF)_3$ (2.94 mmol) dissolved in 50 mL THF was added into the solution at −30° C. and the mixture stirred at ambient temparature for 16 hours. Solvents were removed under a vacuum and the product extracted in toluene, filtered and evaporated. The paramagnetic product was purified by washing with cold pentane and evaporated.

EXAMPLE 11
Synthesis of triazabicyclodec-ene-yl-1-diphenylsilylchloride $C_{19}H_{22}ClN_3Si$

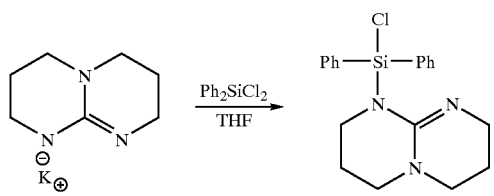

1.5.7-Triaza[4.4.0]bicyclo-dec-5-enyl potassium 3.0 g (16.9 mmol) dissolved in 50 mL of THF was added into a solution of 21 mL (101.5 mmol) of $Ph_2SiCl_2$ in 50 mL THF over 3 hours at ambient temperature. Colour changed from whitish to light yellow. The solution was stirred for 2 hours at ambient temperature after which the mixture containing a gelish precipitate of KCl was filtrated and washed with 2×30 mL of THF. Solvents were removed under vacuum to obtain a slightly viscous liquid. Then 50 mL of pentane was added to the filtrate and the precipitated product separated by filtration and washed with 2×30 mL of more pentane. Yield 5.2 g (87.3%) of white solid. $^1$H-NMR $CDCl_3$ δ: 7.52 (dd, 4H), 7.34 (d, 2H), 7.32 (d, 4H), 3.25 (m, 4H), 3.15 (t, 4H), 1.96 (q, 4H). $^{13}$C-NMR $CDCl_3$ δ: 155.1, 141.0, 134.0, 128.3, 127.2, 46.6, 38.8, 23.2. The EIMS analysis showed the decomposition pattern of the parent ion of the title compound $C_{19}H_{22}ClN_3Si$ $M^+$=355.94 g $mol^{-1}$, frgamentation peaks at 320, 278 and 138. Elemental analysis calc. C 64.11%, H 6.23%, N 11.81%, Cl 9.96%, Si 7.89%; Found C 63.89%, H 6.20%, N 11.97%, Cl 9.90%, Si 7.74%.

EXAMPLE 12
Synthesis of triazabicyclodec-ene-yl-1-diphenylsilyl-tetramethylcyclopentadiene $C_{28}H_{35}N_3Si$

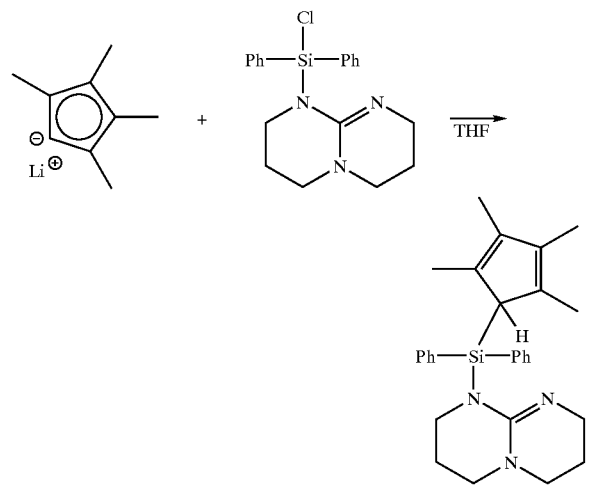

Tetramethylcyclopentadienyl lithium 1.04 g (8.15 mmol) (prepared from tetramethylcyclopentadiene via treatment of n-butyllithium) dissolved in 50 mL THF was added into a solution of triazabicyclodec-ene-yl-1-diphenyl-silylchloride in 50 mL of THF over 20 minutes at −30° C. The mixture was stirred at ambient temperature for 16 hours, after which the solvents were removed under vacuum, the product extracted in pentane, filtered and evaporated. Yield 2.2 g (61.1%) of white solid. The EIMS analysis shows the decomposition pattern of the parent of the title compound $C_{28}H_{35}N_3Si$ $M^+$441.69 g $mol^{-1}$. $^1$H-NMR THF-$d_8$ δ: 7.54 (d, 4H), 7.22 (m, 4H), 7.20 (d, 4H), 4.21 (s, 1H), 3.17 (t, 4H), 3.03 (t, 4H), 1.83 (s, 6H), 1.75 (m, 4H), 1.42 (s, 6H). $^{13}$C-NMR THF-$d_8$ δ: 151.9, 136.8, 136.7, 136.6, 133.3, 128.9, 126.9, 54.8, 48.6, 43.4, 24.7, 14.5, 11.6. Elemental analysis calc. C 76.14%, H 7.99%, N 9.51%, Si 6.36%; Found C 76.04%, H 8.13%, N 9.54%, Si 6.38%.

EXAMPLE 13
Synthesis of triazabicyclodec-ene-yl-1-diphenylsilyl-tetramethylcyclopentadiene chromium dichloride $C_{28}H_{34}Cl_2CrN_3Si$

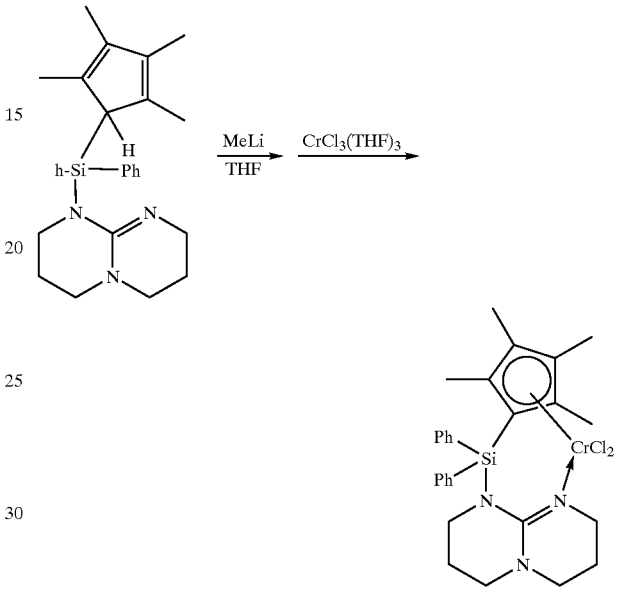

4.6 mL of methyl lithium (8.15 mmol, 1.76 M solution in diethyl ether) was added into a solution of triazabicyclodec-ene-yl-1-diphenylsilyl-tetramethylcyclopentadiene in 50 mL of THF at −30° C. The solution was stirred at ambient temperature for 16 hours. A whitish precipitate formed. Then $CrCl_3(THF)_3$ dissolved in 50 mL of THF (8.15 mmol) was added over 30 minutes at −30° C., and the mixture stirred 16 hours at ambient temperature. The solvent was removed under vacuum and the product extracted in toluene, filtered and evaporated. EIMS M®=563.59 g $mol^{-1}$. Elemental analysis calc. C 59.67%, H 6.08%, N 7.46%, Cl 12.58%, Si 4.98%, Cr 9.23%; Found C 59.42%, H 6.23%, N 7.52%, Cl 12.82%, Si 5.05%, Cr 9.35%.

EXAMPLE 14
Synthesis of Trimethylsiloxycyclopentadiene

Scheme 1.

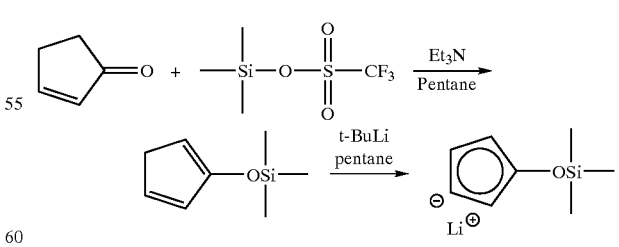

9.1 g (111.0 mmol) of cyclopent-2-en-1-one (Fluka 29827), 11.31 g (111.8 mmol) of triethylamine dried with molecular sieves and 300 mL of dry pentane are mixed at room temperature. Over 13 minutes 24.75 g (111.4 mmol) of trimethylsilyl-trifluoromethylsulfonate (Fluka 91741) is added to the mixture. After stirring for 2.5 hour the supernatant pentane fraction is separated, solvent removed under reduced pressure and the remainder distilled under reduced pressure resulting in an isomer mixture of trimethylsiloxycyclopentadienes. The product is characterised by ¹H-NMR and GC/MS⁺. Trimethylsiloxycyclopentadienyl lithium is prepared as described in the last section of example 3 by using t-BuLi.

Scheme 2.

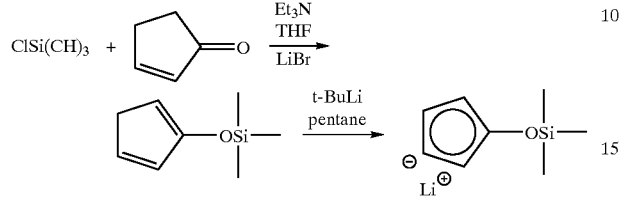

Trimethylsiloxycyclopentadiene can also be synthesised according to the description in Acta. Chem. Scandinavica, 43, 1989, 188–92 (Scheme 2). 1.74 g of LiBr (20 mmol, dried under vacuum at 400° C.) is dissolved in 5.55 g of THF (77 mmol). At −15° C., 1.54 g of chlorotrimethylsilane (15 mmol), 1.23 g of cyclopent-2-en-1-one (15 mmol) and 1.51 g of triethylamine (15 mmol, dry) are added to the solution. After 1 hour at −15° C. and 24 hours at +40° C. the crude product is isolated by low temperature aqous NaCl/NaHCO₃ and pentane extractions. The crude trimethylsiloxycyclopentadienes are purified by distillation under reduced pressure. Trimethylsiloxycyclopentadienyl lithium is prepared as described in the last section of example 3 by using t-BuLi.

EXAMPLE 15
Synthesis of triazabicyclodec-ene-yl-1-diphenylsilyl-trimethylsiloxycyclopentadiene $C_{27}H_{35}N_3OSi_2$

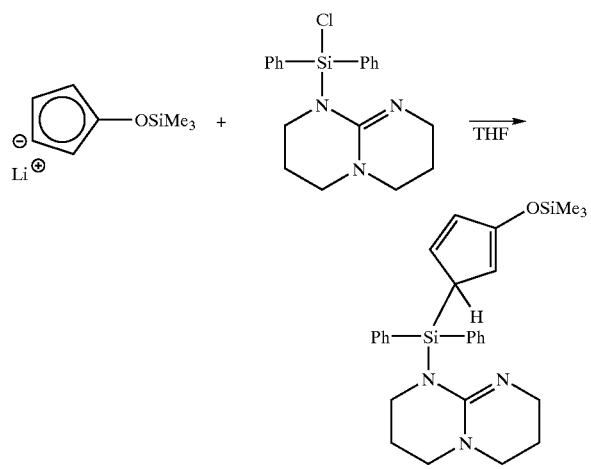

Trimethylsiloxycyclopentadienyl lithium (8.15 mmol) (prepared from trimethylsiloxycyclopentadiene via treatment of t-butyllithium) dissolved in 50 mL THF is added into a solution of triazabicyclodec-ene-yl-1-diphenylsilylchloride in 50 mL of THF over 20 minutes at −30° C. The mixture is stirred at ambient temperature for 16 hours, after which the solvents are removed under vacuum, the product extracted in pentane, filtered and the major kinetically formed isomer with 1,3-substitution pattern of the siloxy and the bridge subtituents on the Cp ring is obtained via recrystallization from cold pentane.

EXAMPLE 16
Synthesis of triazabicyclodec-ene-yl-1-diphenylsilyl-trimethylsiloxycyclopentadienyl chromium dichloride $C_{27}H_{34}Cl_2CrN_3OSi_2$

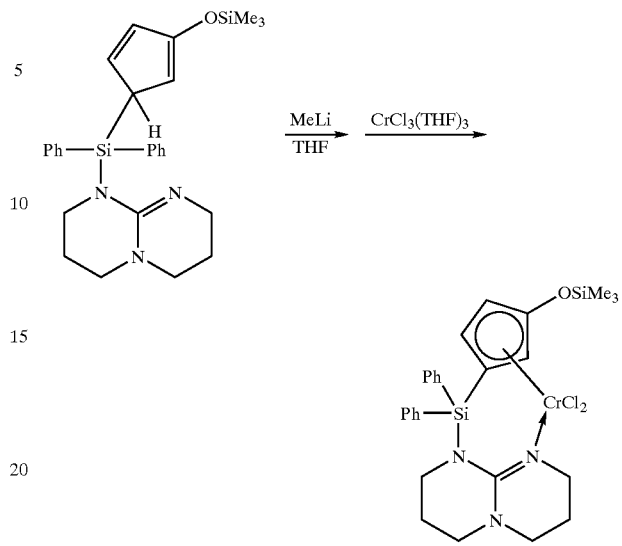

Methyl lithium (8.15 mmol, 1.76 M solution in diethyl ether) is added into a solution of triazabicyclodec-ene-yl-1-diphenylsilyl-tetramethylcyclopentadiene in 50 mL of THF at −30° C. The solution is stirred at ambient temperature for 16 hours. A whitish precipitate forms. Then CrCl₃(THF)₃ dissolved in 50 mL of THF (8.15 mmol) is added over 30 minutes at −30° C., and the mixture stirred 16 hours at ambient temperature. The solvent is removed under vacuum and the product extracted in toluene, filtered and evaporated to give a blue solid product.

EXAMPLE 17
Synthesis of Dipyridin-2-ylmethane $C_{11}H_{10}N_2$

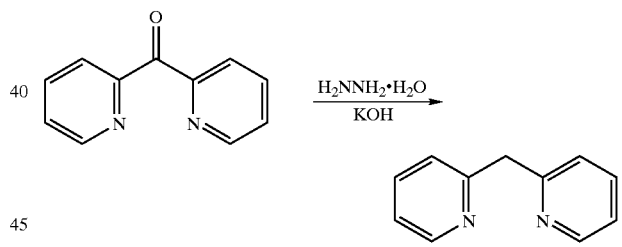

Solid KOH (9.4 g, 167.7 mmol) was dissolved in 15 mL of distilled water and poured into an autoclave reactor (Parr pressure reactor) under nitrogen atmosphere. Di(2-pyridyl)ketone (15.0 g, 81.4 mmol) was weighed and introduced into the reactor. Hydrazine monohydrate (6.1 mL, 185.7 mmol) was poured into the reaction mixture and the reactor closed. The reactor was mounted on a Parr heater unit and the reaction mixture stirred for 18 h at 150° C. at 28 bar. After 1 hour the temperature was 150° C. and the pressure 5 bar. After 18 h heating and stirring the temperature was 151° C. and the pressure inside the reactor 28 bar. After the reaction was complete, the cooled reactor was opened at air atmosphere and the yellowish liquid obtained neutralized with 1M HCl (aq.) and extracted with 3×50 mL chloroform. Organic phase was washed with 3×30 mL of brine and dried over MgSO₄. Solvents were removed in a vacuum and the crude product distilled in a vacuum to obtain a yellow liquid with b.p. 80–85° C./0.06 m bar. Yield: 9.8 g (72%). ¹H-NMR in CDCl₃; δ: 8.48 (m, 2H); 7.51 (m, 2H); 7.19 (t, 2H); 7.04 (m, 2H); 4.29 (s, 2H). EIMS analysis showed parent ion of the title compound $C_{11}H_{10}N_2$ corresponding to molecular weight M⁺=170.21 g mol⁻¹.

EXAMPLE 18
Synthesis of Dipyridin-methan-2-yl-potassium $C_{11}H_9KN_2$

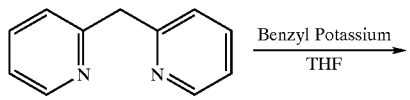

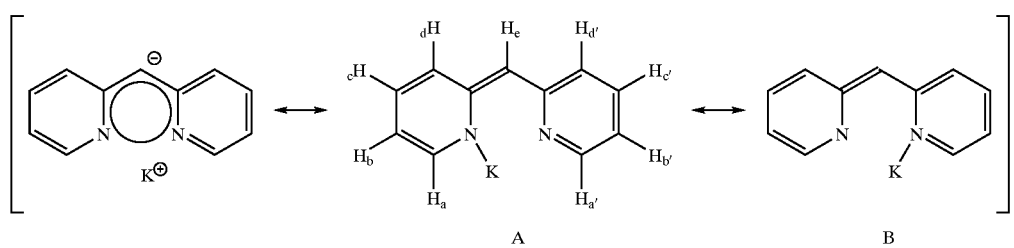

Benzyl potassium 4.0 g (30.5 mmol) was added into a solution of dipyridin-2-ylmethane 5.2 g (30.5 mmol) in 100 mL THF at −70° C. over 10 minutes. The mixture was stirred at ambient temperature for 16 hours after which the bright yellow mixture was filtrated and washed with THF. Solvents were evaporated and the product washed with pentane and evaporated to yield a bright yellow solid which on the basis of the $^1$H-NMR spectrum in DMSO-$d_6$ was [DPM$^-$K$^+$][THF]$_{0.5}$. Yield 5.44 g (73.0%) based the THF complex ($M_w$=244.35 g mol−1). The product decomposed during ETMS analysis. Elemental analysis calculated for [DPM$^{-K+}$][$THF$]$_{0.5}$: C 64.6%, H 4.8%, N 12.0%, K 21.9%. Found: C 63.9%, H 5.36%, N 11.46%, K 16.0%. NMR spectra were recorded at +22.7° C., +50° C. and at +70° C. in DMSO-$d_6$. The complex shows fluxional behaviour in NMR with increasing temperature which is caused by the transition between the two resonance structures A and B. The peaks coalescence at +70° C. The singlet bridgehead proton is exchanged slowly with the methyl deuterium of DMSO-$d_6$ which is seen as an appearing triplet in $^{13}$C-NMR. $^1$H-NMR in DMSO-$d_6$ at +70° C. δ: 8.20 and 6.25 (broad coalesence peaks, 2H, from H$_a$++H$_{a'}$), 7.65 (d, 2H, from H$_d$++H$_{d'}$), 6.78 (broad, 2H, from H$_b$++H$_{b'}$), 5.76 (broad, 2H, from H$_c$++H$_{c'}$), 4.62 (S, 1H, exchangeable proton H$_e$). $^{13}$C-NMR in DMSO-$d_6$ at δ: 160.2, 147.9, 147.8, 132.3, 131.2, 116.9, 114,3, 105.3, 103.3, triplet 87.2 from exchanged CH$_e$++DMSO-$d_6$. $^{13}$C-CPMAS δ: 163, 150, 138, 119, 109, 82.

EXAMPLE 19
Synthesis of triazabicyclodec-ene-yl-1-dimethylsilyl-dipyridin-methane $C_{20}H_{27}N_5Si$

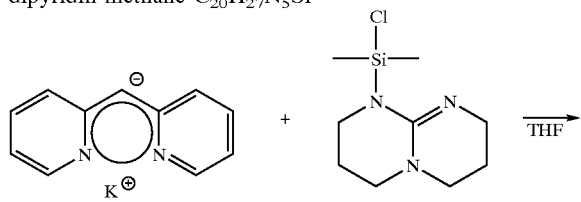

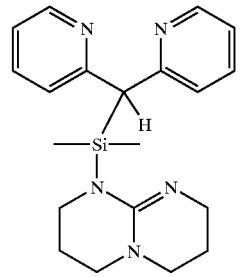

Dipyridin-methan-2-yl-potassium 2.62 g (12.6 mmol) dissolved in 100 mL THF of was added into a solution of triazabicyclodec-ene-yl-1-dimethylsilylchloride 2.90 g (12.6 mmol) in 100 mL of THF over 40 minutes at −70° C. The mixture was stirred at ambient temperature for 16 hours. Solvent was evaporated under vacuum, the product extracted in toluene, filtrated and washed with more toluene. Solvent was removed under vacuum and the product grinded in glove box. The product was purified by washing with cold pentane. Pentane solubles were filtered off and the product evaporated under vacuum. Yield 3.7 g (80.0%) of yellow solid. EIMS analysis showed the decomposition pattern of parent ion of the title compound $C_{20}H_{27}N_5Si$ corresponding to molecular weight M$^+$=365.55 g mol$^{-1}$, fragmentation peaks at 335, 258, 196, 169, 138. $^1$H-NMR in THF-$d_8$ δ: 8.45 (d, 2H), 7.45 (dd, 2H), 7.44 (d, 2H) 6.99 (t, 2H). 4.92 (s, 1H), 3.06 (t, 4H), 2.86 (t, 4H), 1.61 (q, 4H), 0.16 (s, 6H). Elemental analysis calculated: C 65.7%, H 7.44%, N 19.2%. found: C 63.8%, H 6.8%, N 16.6%.

EXAMPLE 20
Synthesis of Triazabicyclodec-ene-yl-1-dimethylsilyl dipyridylmethan-yl Chromium Dichloride $C_{20}H_{28}Cl_2CrN_5Si$

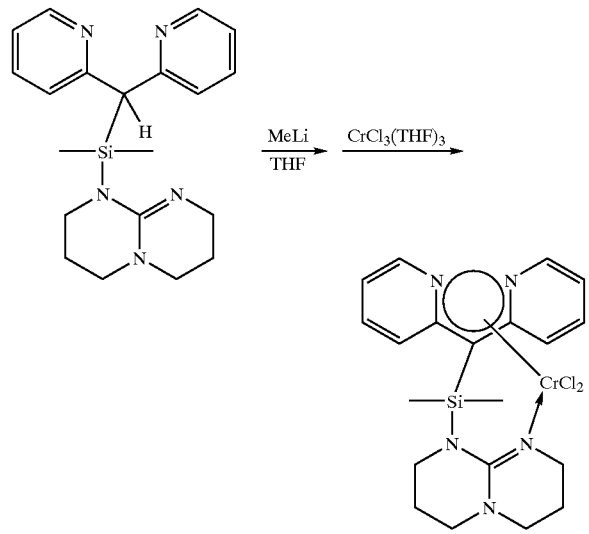

1.9 mL methyl lithium (3.7 mmol, 1.94 M solution in diethyl ether) was added into a solution of triazabicyclodec-ene-yl-1-dimethylsilyl dipyridylmethane 1.33 g (3.6 mmol) dissolved in 100 mL THF at −30° C. over 5 minutes. The mixture was stirred at ambient temperature for 2 hours. $CrCl_3(THF)_3$ (3.6 mmol) was added at −30° C. over 30 minutes and the solution stirred at ambient temperature over 16 hours. Solvents were removed under vacuum, the product extracted in toluene, filtered and evaporated. The product was purified by washing with cold dichloromethane and pentane. Yield 0.2 g (25.5%) of dark brown tar. The product decomposed during EIMS analysis. The product was paramagnetic, NMR identification could not be obtained.

EXAMPLE 21
Synthesis of Triazacyclodec-ene-yl-1-dimethylsilyl dipyridylmethan-yl Chromium Dichloride $C_{20}H_{28}Cl_2TiN_5Si$

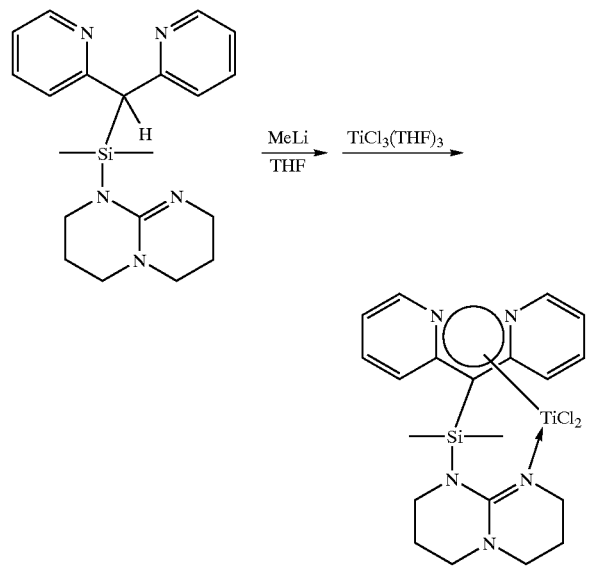

0.8 mL methyl lithium (1.64 mmol, 1.94 M solution in diethyl ether) was added into a solution of triazabicyclodec-ene-yl-1-dimethylsilyl dipyridylmethane 0.60 g (1.64 mmol) dissolved in 70 mL THF at −30° C. over 5 minutes. The mixture was stirred at ambient temperature for 16 hours. $TiCl_3(THF)_3$ (1.64 mmol) was added at −70° C. over 20 minutes and the solution stirred at ambient temperature over 3 hours. Solvents were removed under vacuum, the product extracted in toluene, filtered and evaporated. The product was purified by washing with cold dichloromethane and pentane. Yield 0.5 g (64.9%) of dark brown tar. The product decomposed during EIMS analysis. The product was paramagnetic, NMR identification could not be obtained.

EXAMPLE 22
Dimethylmethylene cyclopentadienyl triazabicyclodec-ene-yl-1 potassium $C_{15}H_{22}KN_3$

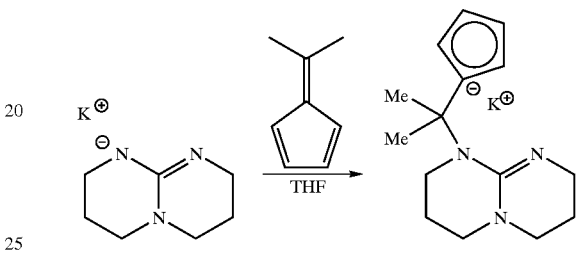

Dimethylfulvene 1.8 mL (14.7 mmol) was added to (1.5.7-triaza[4.4.0]bicyclo-dec-5-enyl) potassium 2.6 g (14.7 mmol) in THF at 0° C. over one hour. The mixture was stirred at ambient temperature overnight, and the solvent removed under vacuum. The product was washed with pentane and dried under vacuum to afford 3.2 g (79.05%) or light grey solid. $^1$H-NMR in THF δ: 5.92 (dd, 2H), 5.65 (dd, 2H), 3.10 (t, 4H), 3.04 (t, 4H), 3.81 (s, 6H), 3.61 (m, 4H). $^{13}$C-NMR in THF δ: 151.0, 142.4, 121.9, 105.8, 102.9, 48.2, 41.8, 23.6, 22.2. MS analysis showed the decomposition pattern of the parent title compound. No M$^+$ was detected due to the decomposition of the sample during the analysis. Elemental analysis calculated C 63.56% H 7.82% N 14.82% K 13.79%, found C 63.36% H 7.75% N 15.07% K 13.55%.

EXAMPLE 23
Dimethylmethylene cyclopentadienyl triazabicyclodec-ene-yl-1 chromium dichloride $C_{15}H_{22}Cl_2CrN_3$.

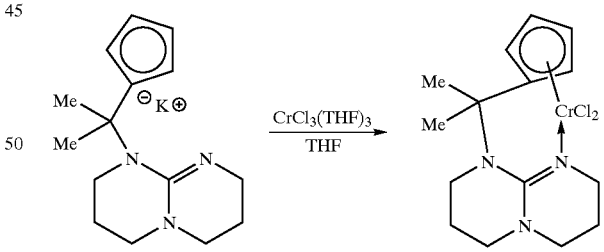

Dimethylmethylene cyclopentadienyl triazabicyclodec-ene-yl-1potassium $CrCl_3(THF)_3$ 3.4 g (9.08 mmol) in THF was added to a solutiuon of triazabicyclodec-ene-yl-1-dimethylmethylene potassium 2.6 g (9.08 mmol) in THF at −30° C. over a period of 30 minutes. The mixture was stirred overnight at ambient temperature. Solvent was removed under reduced pressure and the product extracted in toluene, filtrated and dried under vacuum. The filtrate was then extracted in dichloromethane, filtrated, and dried again under vacuum. The product was washed with pentane to afford pure dark blue microcrystalline solid 2.3 g (68.7%). EIMS analysis showed the decomposition pattern of the title compound, $M^+=367.26$ g mol$^{-1}$ peak was not detected due to decomposition during analysis. Elemental analysis calculated C 49.06% H 6.04% N 11.44% Cl 19.31% Cr 14.16%, found C 47.81% H 6.06% N 13.05% Cl 18.80% Cr 13.60%.

Polymerization Examples

TABLE 1

Ethylene homopolymerization test results using homogeneous catalysts

| Complex | Act. HOPO | $M_w \times 10^3$ | $M_w/M_n$ | Cryst. % | m.p. °C. | Al/M |
|---|---|---|---|---|---|---|
| Example 6 Me$_2$Si(Me$_2$Cp-OSiMe$_2$—tBu)(TAB)CrCl$_2$ | 2778 | n.d. | n.d. | 53.6 | 134.3 | 757 |
| Example 8 Me$_2$Si(Cp-OSi—iPr$_3$)(TAB)CrCl$_2$ | 395 | 977 | 30.2 | 57.1 | 135.1 | 778 |
| Example 13 Ph$_2$Si(Me$_4$Cp)(TAB)CrCl$_2$ | 1048 | 412 | 27.8 | 66.7 | 133.2 | 1000 |
| Example 10 Me$_2$Si(Flu)(TAB)CrCl$_2$ | 50 | 272 | 6.6 | 58.9 | 134.2 | 1000 |

$^1$Al/M ratio 700–1000, MAO, temp +60° C., C$_2$ = 10 bar.
n.d. = not determined (too high $M_w$ for GPC measurement device).
Activity in [kg PE/g met. h$^{-1}$]

TABLE 2

Ethylene homopolymerization using homogeneous catalysts and hydrogen

| Complex | Act. HOPO/H$_2$ | $M_w \times 10^3$ | $M_w/M_n$ | Cryst. % | m.p. °C. | Al/M |
|---|---|---|---|---|---|---|
| Example 6 Me$_2$Si(Me$_2$Cp-OSiMe$_2$—tBu)(TAB)CrCl$_2$ | 1902$^1$ | 198 | 7.4 | 71.1 | 132.5 | 1000 |
| Example 13 Ph$_2$Si(Me$_4$Cp)(TAB)CrCl$_2$ | 2628.1 | — | — | — | — | — |
| Example 8 Me$_2$Si(Cp-OSi—iPr$_3$)(TAB)CrCl$_2$ | 486 | 192 | 8.1 | 67.3 | 135.7 | 763 |

$^1$Amount of hydrogen fed to the 2 L reactor was 0.6 bar/677 mL
$^2$Amount of hydrogen fed to the 2 L reactor was 0.3 bar/677 mL.
n.d. = not determined (too high $M_w$ for GPC measurement device).
Activity in [kg PE/g met. h$^{-1}$].
Temp. +60° C.

TABLE 3

Copolymerization of ethylene and 1-hexene using homogeneous catalysts

| Complex | Act. COPO |
|---|---|
| Example 13 Ph$_2$Si(Me$_4$Cp) (TAB) CrCl$_2$ | 2713.5 |
| Example 23 Me$_2$C(Cp) (TAB) CrCl$_2$ | 91.62 |

Activity in [kg PE/g met. h$^{-1}$]

TABLE 4

Polymer double bond analysis results of the ethylene homopolymers[#]

| Complex | t-vinylene | vinyl | vinylidene |
|---|---|---|---|
| Example 6 Me$_2$Si (Me$_2$Cp-OSiMe$_2$—tBu) (TAB) CrCl$_2$ | 0.11 | 0.09 | 0.03 |
| Example 8 Me$_2$Si (Cp-OSi—iPr$_3$) (TAB) CrCl$_2$ | n.d. | n.d. | n.d. |
| Example 13 Ph$_2$Si (Me$_4$Cp) (TAB) CrCl$_2$ | 0.21 | 0.71 | 0.12 |
| Example 10 Me$_2$Si (Flu) (TAB) CrCl$_2$ | 0 | 0.18 | 0.05 |

[#]Unit is double bonds per 1000 carbon atoms (C═C/1000C).

TABLE 5

Propylene polymerisations. Al/Cr ratio 1000, polymerisation time 90 minutes. 5 bar propylene pressure (60° C.). Cocatalyst MAO & TIBA (tetraisobutylalumoxane) 150 μL, 1100 g propylene.

| Complex | Yield of Polymer | Notes |
|---|---|---|
| Example 6 | 0.7 g | |
| Example 6 | 1.4 | 6 g Ethylene added |

TABLE 6

Analysis results of the polymers

| Code | Run Type | DSC (%) | DSC, TCR1 (° C.) | TM1 (° C.) | MN (g/mol) | MW (g/mol) | MW/MN | MZ (g/mol) | MFR21 | T-VINYL | VINYL | VINYLIDEN |
|---|---|---|---|---|---|---|---|---|---|---|---|---|
| 8 | HOPO60 | 57.1 | 115.9 | 135.1 | 32300 | 977000 | 30.2 | 6302000 | 0.03 | | | |
| 8 | HOPO80 | 64 | 116.2 | 129.9 | | | | | not done | 0.16 | 1.46 | 0.6 |
| 8 | HOPO/H260 | 67.3 | 116.3 | 135.7 | 23600 | 192000 | 8.1 | 1392000 | 14.5 | 0 | 0.27 | 0.1 |
| 6 | HOPO60 | 53.6 | 115.9 | 134.3 | | | | | 0.008 | 0.11 | 0.09 | 0.0 |
| 6 | HOPO80 | 72.3 | 118.2 | 131.3 | | | | | 28.4 | 0.84 | 0.68 | 0.2 |
| 6 | HOPO/H260 | 71.1 | 119 | 132.5 | 26900 | 198000 | 7.4 | 3553000 | 42.5 | 0.06 | 0.09 | 0.0 |

Heterogeneous polymerisation test result of compound 20 using silica

| Pol type | Activity of cat (KgPol/g cat h) | Activity of metal KgPol/g met h | Al/Me | Flowmeter C2 (g) | Temperature (° C.) | CR1 (%) | DSC TCR1 (° C.) | TM1 (° C.) |
|---|---|---|---|---|---|---|---|---|
| HDPE | 0.01 | 4.6 | 200 | 28 | 60 | 49.1 | 119.9 | 113.4 |
| HDPE | 0.00 | 4.3 | 200 | 24 | 80 | 51.3 | 120 | 132.5 |

| | GPC-Normal | | | MFR | | FTIR, (C=C/1000C) | | |
|---|---|---|---|---|---|---|---|---|
| MN1 | MW1 | MW1/MN1 | MZ1 | 21.6 KG | T-VINYLENE | VINYL | | VINYLIDENE |
| 204600 | 1899000 | 9.3 | 6079000 | not done | X | X | | X |
| 19000 | 1742000 | 91.7 | 9030000 | not done | X | X | | X |

What is claimed is:

1. A compound of formula (I)

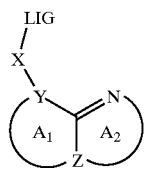

wherein
LIG represents an $\eta^5$-ligand substituted by a group $R_1$ and a group $(R")_m$;
X represents a 1 to 3 atom bridge;
Y represents a nitrogen or phosphorus atom;
Z represents a carbon, silicon, nitrogen or phosphorus atom;
the ring denoted by $A_1$ is an optionally substituted, optionally saturated or unsaturated 5 to 12 membered heterocyclic ring;
the ring denoted by $A_2$ is an optionally substituted, unsaturated 5 to 12 membered heterocyclic ring;
$R_1$ represents hydrogen, R" or a group $OSiR'_3$;
each R', which may be the same or different is a $R^+$, $OR^+$, $SR^+$, $NR^+_2$ or $PR^+_2$ group where each $R^+$ is a $C_{1-16}$ hydrocarbyl group, a tri-$C_{1-8}$hydrocarbylsilyl group or a tri-$C_{1-8}$hydrocarbylsiloxy group;
each R", which may be the same or different is a ring substituent which does not form a σ-bond to a metal η-bonded by the bicyclic ring; and
m is zero or an integer between 1 and 3.

2. A compound as claimed in claim 1 wherein Z represents a nitrogen atom.

3. A compound as claimed in claim 1 or 2 wherein Y represents a nitrogen atom.

4. A compound as claimed in claim 1 wherein $A_1$ and $A_2$ are five or six-membered rings.

5. A compound as claimed in claim 1 or 4 wherein $A_1$ and $A_2$ are unsubstituted and comprise only 1 double bond.

6. A compound as claimed in claim 1 wherein $A_1$ and $A_2$ represent

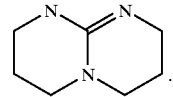

7. A compound as claimed in claim 1 wherein LIG comprises a dipyridymethanyl, cyclopentadienyl, fluorenyl or indenyl ligand.

8. A compound as claimed in claim 1 wherein R" represents hydrogen, $R^+$, $OR^+$, $SR^+$, $NR^+_2$ or $PR^+_2$ group where each $R^+$ is a $C_{1-16}$ hydrocarbyl group, a tri-$C_{1-8}$ hydrocarbylsilyl group or a tri-C1.8hydrocarbylsiloxy group.

9. A compound as claimed in claim 7 or 8 wherein LIG represents cyclopentadienyl and $R_1$ represents $OSiR'_3$ each R' being a $C_{1-12}$ hydrocarbyl group.

10. A compound as claimed in claim 9 wherein R" represents $C_{1-6}$ alkyl.

11. A compound as claimed in claim 1 wherein LIG represents

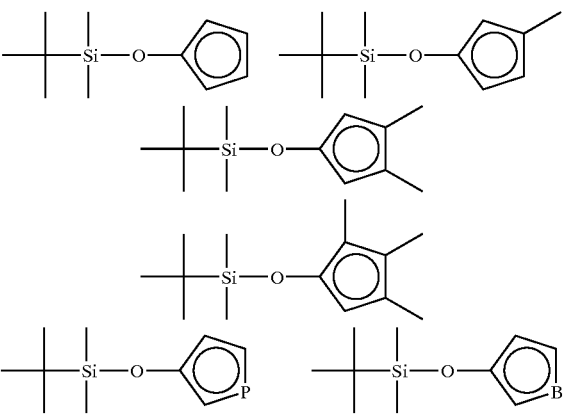

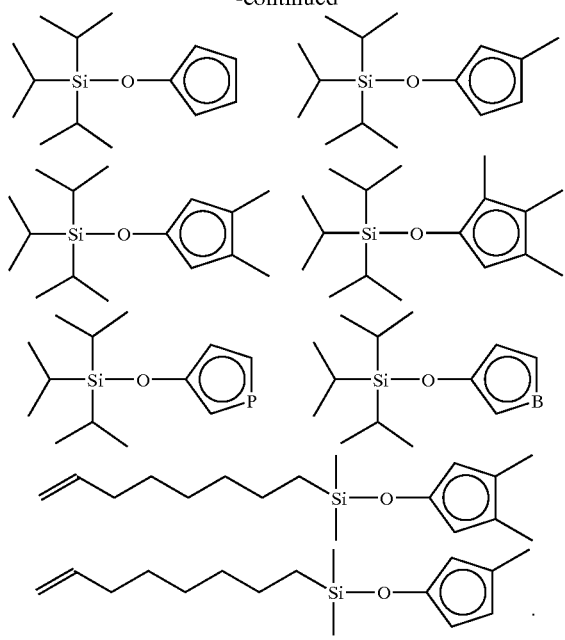

12. A compound as claimed in claim 1 wherein m is 3, LIG is a cyclopentadienyl and R" is methyl.

13. A compound as claimed in claim 1 wherein X is a one atom bridge comprising Si or a one atom bridge comprising a carbon atom.

14. A compound as claimed in claim 1 wherein LIG represents fluorenyl, indenyl or dipyridymethanyl and R' and R" represent hydrogen.

15. A compound as claimed in claim 1 of formula

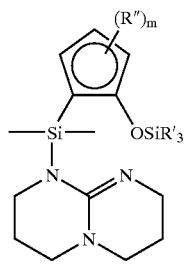

16. A procatalyst comprising a compound of formula (I) as claimed in claim 1 coordinated to a metal ion of group 3 to 7, the Y atom not being coordinated to the metal.

17. A procatalyst as claimed in claim 16 wherein said metal ion is an ion of Cr or Ti.

18. A procatalyst as claimed in claim 16 or 17 wherein said metal is additionally coordinated to a halogen σ-ligand.

19. A procatalyst as claimed in claim 16 or 17 wherein at least one of the atoms N or Z or the double bond of the bicyclic ring is coordinated to the metal ion.

20. A procatalyst as claimed in claim 19 wherein the group LIG and the atom N are coordinated to the metal ion.

21. An olefin polymerisation catalyst system comprising or produced by reaction of (1) a procatalyst as claimed in claim 16 and (2) a cocatalyst.

22. A process for olefin polymerisation comprising polymerising an olefin in the presence of a catalyst system as described in claim 21.

23. A process for the preparation of a procatalyst, said process comprising metallating with a group 3 to 7 transition metal a compound of formula (I)

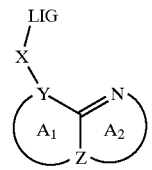

wherein LIG represents an $\eta^5$-ligand substituted by a group $R_1$ and a group $(R")_m$;

X represents a 1 to 3 atom bridge;

Y represents a nitrogen or phosphorus atom;

Z represents a carbon, silicon, nitrogen or phosphorus atom;

the ring denoted by $A_1$ is an optionally substituted, optionally saturated or unsaturated 5 to 12 membered heterocyclic ring;

the ring denoted by $A_2$ is an optionally substituted, unsaturated 5 to 12 membered heterocyclic ring;

$R_1$ represents hydrogen, R" or a group $OSiR'_3$;

each R, which may be the same or different is a $R^+$, $OR^+$, $SR^+$, $NR^+_2$ or $Pr^+_2$ group where each $R^+$ is a $C_{1-16}$ hydrocarbyl group, a tri-$C_{1-8}$hydrocarbylsilyl group or a tri-$C_{1-8}$hydrocarbylsiloxy group;

each R", which may be the same or different is a ring substituent which does not form a σ-bond to a metal η-bonded by the bicyclic ring; and m is zero or an integer between 1 and 3.

* * * * *